(12) United States Patent
Davis et al.

(10) Patent No.: US 9,121,059 B2
(45) Date of Patent: Sep. 1, 2015

(54) NANOPORE-BASED SINGLE MOLECULE CHARACTERIZATION

(75) Inventors: Randall W. Davis, Pleasanton, CA (US); Roger J. A. Chen, Saratoga, CA (US)

(73) Assignee: Genia Technologies, Inc., Mountain View, CA (US)

( * ) Notice: Subject to any disclaimer, the term of this patent is extended or adjusted under 35 U.S.C. 154(b) by 808 days.

(21) Appl. No.: 13/333,915

(22) Filed: Dec. 21, 2011

(65) Prior Publication Data

US 2012/0160688 A1 Jun. 28, 2012

Related U.S. Application Data

(60) Provisional application No. 61/426,322, filed on Dec. 22, 2010, provisional application No. 61/426,323, filed on Dec. 22, 2010.

(51) Int. Cl.
| | |
|---|---|
| *C12Q 1/68* | (2006.01) |
| *G01N 33/487* | (2006.01) |
| *B82Y 15/00* | (2011.01) |
| *G01N 27/447* | (2006.01) |
| *B82Y 10/00* | (2011.01) |

(52) U.S. Cl.
CPC .............. *C12Q 1/6869* (2013.01); *B82Y 15/00* (2013.01); *C12Q 1/6816* (2013.01); *G01N 27/447* (2013.01); *G01N 33/48721* (2013.01); *B82Y 10/00* (2013.01); *Y10S 977/924* (2013.01)

(58) Field of Classification Search
None
See application file for complete search history.

(56) References Cited

U.S. PATENT DOCUMENTS

| | | | |
|---|---|---|---|
| 2,656,508 | A | 10/1953 | Coulter |
| 4,121,192 | A | 10/1978 | Wilson |
| 4,859,945 | A | 8/1989 | Stokar |
| 5,198,543 | A | 3/1993 | Blanco et al. |
| 5,302,509 | A | 4/1994 | Cheeseman |
| 5,308,539 | A | 5/1994 | Koden et al. |
| 5,457,342 | A | 10/1995 | Herbst, II |
| 5,569,950 | A | 10/1996 | Lewis et al. |
| 5,576,204 | A | 11/1996 | Blanco et al. |
| 5,756,355 | A | 5/1998 | Lang et al. |
| 5,770,367 | A | 6/1998 | Southern et al. |
| 5,795,782 | A | 8/1998 | Church et al. |
| 5,804,386 | A | 9/1998 | Ju |
| 5,814,454 | A | 9/1998 | Ju |
| 5,869,244 | A | 2/1999 | Martin et al. |
| 5,876,936 | A | 3/1999 | Ju |
| 5,912,155 | A | 6/1999 | Chatterjee et al. |
| 5,939,301 | A | 8/1999 | Hughes, Jr. et al. |
| 5,952,180 | A | 9/1999 | Ju |
| 5,981,733 | A | 11/1999 | Gamble et al. |
| 6,012,291 | A | 1/2000 | Ema |
| 6,014,213 | A | 1/2000 | Waterhouse et al. |
| 6,015,714 | A | 1/2000 | Baldarelli et al. |
| 6,046,005 | A | 4/2000 | Ju et al. |
| 6,082,115 | A | 7/2000 | Strnad |
| 6,210,896 | B1 | 4/2001 | Chan |
| 6,217,731 | B1 | 4/2001 | Kane et al. |
| 6,232,103 | B1 | 5/2001 | Short |
| 6,255,083 | B1 | 7/2001 | Williams |
| 6,261,797 | B1 | 7/2001 | Sorge et al. |
| 6,265,193 | B1 | 7/2001 | Brandis et al. |
| 6,321,101 | B1 | 11/2001 | Holmstrom |
| 6,362,002 | B1 | 3/2002 | Denison et al. |
| 6,383,749 | B2 | 5/2002 | Bochkariov et al. |
| 6,399,320 | B1 | 6/2002 | Markau et al. |
| 6,399,335 | B1 | 6/2002 | Kao et al. |
| 6,413,792 | B1 | 7/2002 | Sauer et al. |
| 6,485,703 | B1 | 11/2002 | Cote et al. |
| 6,607,883 | B1 | 8/2003 | Frey et al. |
| 6,616,895 | B2 | 9/2003 | Dugas et al. |
| 6,627,748 | B1 | 9/2003 | Ju et al. |
| 6,664,079 | B2 | 12/2003 | Ju et al. |
| 6,673,615 | B2 | 1/2004 | Denison et al. |
| 6,686,997 | B1 | 2/2004 | Allen |
| 6,699,719 | B2 | 3/2004 | Yamazaki et al. |
| 6,723,513 | B2 | 4/2004 | Lexow |
| 6,746,594 | B2 | 6/2004 | Akeson et al. |
| 6,762,048 | B2 | 7/2004 | Williams |
| 6,794,177 | B2 | 9/2004 | Markau et al. |
| 6,800,933 | B1 | 10/2004 | Mathews et al. |

(Continued)

FOREIGN PATENT DOCUMENTS

| | | |
|---|---|---|
| WO | WO 91/06678 A1 | 5/1991 |
| WO | WO 93/21340 A1 | 10/1993 |

(Continued)

OTHER PUBLICATIONS

Wanunu et al, Biophys. J. 95: 4716 (2008).*
Bezrukov, et al. Neutral polymers in the nanopores of alamethicin and alpha-hemolysin. Biologicheskie Membrany 2001, 18, 451-455.
Chandler, et al. Membrane surface dynamics of DNA-threaded nanopores revealed by simultaneous single-molecule optical and ensemble electrical recording. Langmuir. Feb. 3, 2004;20(3):898-905.
Henrickson, et al. Driven DNA transport into an asymmetric nanometer-scale pore. Phys Rev Lett. Oct. 2, 2000;85(14):3057-60.
Ju, et al. Energy transfer primers: a new fluorescence labeling paradigm for DNA sequencing and analysis. Nat Med. Feb. 1996;2(2):246-9.
Kasianowicz. Nanometer-scale pores: potential applications for analyte detection and DNA characterization. Dis Markers. 2002;18(4):185-91.
Li, et al. Ion-beam sculpting at nanometre length scales. Nature. Jul. 12, 2001;412(6843):166-9.
Lundquist, et al. A new tri-orthogonal strategy for peptide cyclization. Org Lett. Sep. 19, 2002;4(19):3219-21.
Perkins, et al. Relaxation of a single DNA molecule observed by optical microscopy. Science. May 6, 1994;264(5160):822-6.
Rief, et al. Sequence-dependent mechanics of single DNA molecules. Nat Struct Biol. Apr. 1999;6(4):346-9.

(Continued)

*Primary Examiner* — James Martinell
(74) *Attorney, Agent, or Firm* — Victoria L. Boyd

(57) ABSTRACT

The present invention relates to a method of using nanopore to obtain sequence information of an unknown structure (unknown DNA) in a ss test DNA. The method comprises using speed bump to stall the ss test DNA in the nanopore at random positions of the ss test DNA to obtain sequence information of each and every nucleotides of the unknown DNA, and to construct the whole sequence of the unknown DNA. The present invention also relates to a novel method of trapping a ss test DNA in a nanopore using two bulky structures formed under different conditions (e.g. different temperature), and the bulky structures are able to keep the ss test DNA trapped in a nanopore at a working temperature.

38 Claims, 14 Drawing Sheets

(56) References Cited

U.S. PATENT DOCUMENTS

| | | |
|---|---|---|
| 6,824,659 B2 | 11/2004 | Bayley et al. |
| 6,880,346 B1 | 4/2005 | Tseng et al. |
| 6,891,278 B2 | 5/2005 | Muller et al. |
| 6,916,665 B2 | 7/2005 | Bayley et al. |
| 6,952,651 B2 | 10/2005 | Su |
| 7,033,762 B2 | 4/2006 | Nelson et al. |
| 7,041,812 B2 | 5/2006 | Kumar et al. |
| 7,052,839 B2 | 5/2006 | Nelson et al. |
| 7,057,026 B2 | 6/2006 | Barnes et al. |
| 7,074,597 B2 | 7/2006 | Ju |
| 7,153,672 B1 | 12/2006 | Eickbush et al. |
| 7,189,503 B2 | 3/2007 | Akeson et al. |
| 7,223,541 B2 | 5/2007 | Fuller et al. |
| 7,229,799 B2 | 6/2007 | Williams |
| 7,233,541 B2 | 6/2007 | Yamamoto et al. |
| 7,238,485 B2 | 7/2007 | Akeson et al. |
| 7,244,602 B2 | 7/2007 | Frey et al. |
| 7,279,337 B2 | 10/2007 | Zhu |
| 7,321,329 B2 | 1/2008 | Tooyama et al. |
| 7,345,159 B2 | 3/2008 | Ju et al. |
| 7,361,466 B2 | 4/2008 | Korlach et al. |
| 7,368,668 B2 | 5/2008 | Ren et al. |
| 7,405,281 B2 | 7/2008 | Xu et al. |
| 7,446,017 B2 | 11/2008 | Liu et al. |
| 7,452,698 B2 | 11/2008 | Sood et al. |
| 7,622,279 B2 | 11/2009 | Ju |
| 7,622,934 B2 | 11/2009 | Hibbs et al. |
| 7,625,701 B2 | 12/2009 | Williams et al. |
| 7,626,379 B2 | 12/2009 | Peters et al. |
| 7,635,578 B2 | 12/2009 | Ju et al. |
| 7,710,479 B2 | 5/2010 | Nitta et al. |
| 7,713,698 B2 | 5/2010 | Ju et al. |
| 7,727,722 B2 | 6/2010 | Nelson et al. |
| 7,745,116 B2 | 6/2010 | Williams |
| 7,777,013 B2 | 8/2010 | Xu et al. |
| 7,777,505 B2 | 8/2010 | White et al. |
| 7,790,869 B2 | 9/2010 | Ju et al. |
| 7,871,777 B2 | 1/2011 | Schneider et al. |
| 7,883,869 B2 | 2/2011 | Ju et al. |
| 7,897,738 B2 | 3/2011 | Brandis et al. |
| 7,906,371 B2 | 3/2011 | Kim et al. |
| 7,924,335 B2 | 4/2011 | Itakura et al. |
| 7,939,259 B2 | 5/2011 | Kokoris et al. |
| 7,939,270 B2 | 5/2011 | Holden et al. |
| 7,947,454 B2 | 5/2011 | Akeson et al. |
| 7,948,015 B2 | 5/2011 | Rothberg et al. |
| 7,973,146 B2 | 7/2011 | Shen et al. |
| 7,982,029 B2 | 7/2011 | Ju et al. |
| 7,989,928 B2 | 8/2011 | Liao et al. |
| 8,022,511 B2 | 9/2011 | Chiu et al. |
| 8,058,030 B2 | 11/2011 | Smith et al. |
| 8,058,031 B2 | 11/2011 | Xu et al. |
| 8,058,414 B2 | 11/2011 | Menchen et al. |
| 8,088,575 B2 | 1/2012 | Ju et al. |
| 8,133,672 B2 | 3/2012 | Bjornson et al. |
| 8,137,569 B2 | 3/2012 | Harnack et al. |
| 8,148,516 B2 | 4/2012 | Williams et al. |
| 8,192,961 B2 | 6/2012 | Williams |
| 8,252,911 B2 | 8/2012 | Bjornson et al. |
| 8,257,954 B2 | 9/2012 | Clark et al. |
| 8,298,792 B2 | 10/2012 | Ju et al. |
| 8,324,914 B2 | 12/2012 | Chen et al. |
| 8,541,849 B2 | 9/2013 | Chen |
| 2003/0027140 A1 | 2/2003 | Ju et al. |
| 2003/0054360 A1 | 3/2003 | Gold et al. |
| 2003/0101006 A1 | 5/2003 | Mansky et al. |
| 2003/0166282 A1 | 9/2003 | Brown et al. |
| 2003/0198982 A1 | 10/2003 | Seela et al. |
| 2004/0122335 A1 | 6/2004 | Sackellares et al. |
| 2004/0185466 A1 | 9/2004 | Ju et al. |
| 2005/0032081 A1 | 2/2005 | Ju et al. |
| 2005/0091989 A1 | 5/2005 | Leija et al. |
| 2005/0127035 A1 | 6/2005 | Ling |
| 2005/0186576 A1 | 8/2005 | Chan et al. |
| 2005/0208574 A1 | 9/2005 | Bayley et al. |
| 2005/0221351 A1 | 10/2005 | Ryu |
| 2005/0239194 A1 | 10/2005 | Takahashi et al. |
| 2006/0057565 A1 | 3/2006 | Ju et al. |
| 2006/0105461 A1 | 5/2006 | Tom-Moy et al. |
| 2006/0115951 A1 | 6/2006 | Mosley |
| 2006/0252038 A1 | 11/2006 | Ju |
| 2006/0278992 A1 | 12/2006 | Trezza et al. |
| 2007/0173731 A1 | 7/2007 | Meka et al. |
| 2007/0190542 A1 | 8/2007 | Ling et al. |
| 2007/0196846 A1 | 8/2007 | Hanzel et al. |
| 2007/0275387 A1 | 11/2007 | Ju |
| 2008/0101988 A1 | 5/2008 | Kang et al. |
| 2008/0108082 A1 | 5/2008 | Rank et al. |
| 2008/0199932 A1 | 8/2008 | Hanzel et al. |
| 2008/0218184 A1 | 9/2008 | White et al. |
| 2008/0221806 A1 | 9/2008 | Bryant et al. |
| 2008/0286768 A1 | 11/2008 | Lexow |
| 2008/0318245 A1 | 12/2008 | Smirnov |
| 2009/0029477 A1 | 1/2009 | Meller et al. |
| 2009/0066315 A1 | 3/2009 | Hu et al. |
| 2009/0073293 A1 | 3/2009 | Yaffe et al. |
| 2009/0087834 A1 | 4/2009 | Lexow et al. |
| 2009/0099786 A1 | 4/2009 | Oliver et al. |
| 2009/0102534 A1 | 4/2009 | Schmid et al. |
| 2009/0136958 A1 | 5/2009 | Gershow et al. |
| 2009/0167288 A1 | 7/2009 | Reid et al. |
| 2009/0215050 A1 | 8/2009 | Jenson |
| 2009/0263791 A1 | 10/2009 | Ju et al. |
| 2009/0269759 A1 | 10/2009 | Menchen et al. |
| 2009/0298072 A1 | 12/2009 | Ju |
| 2009/0325154 A1 | 12/2009 | Ju et al. |
| 2010/0025238 A1 | 2/2010 | Gottlieb et al. |
| 2010/0025249 A1 | 2/2010 | Polonsky et al. |
| 2010/0035260 A1 | 2/2010 | Olasagati et al. |
| 2010/0047802 A1 | 2/2010 | Bjorson et al. |
| 2010/0072080 A1 | 3/2010 | Karhanek et al. |
| 2010/0075328 A1 | 3/2010 | Bjornson et al. |
| 2010/0075332 A1 | 3/2010 | Patel et al. |
| 2010/0078777 A1 | 4/2010 | Barth et al. |
| 2010/0092952 A1 | 4/2010 | Ju et al. |
| 2010/0093555 A1 | 4/2010 | Bjornson et al. |
| 2010/0121582 A1 | 5/2010 | Pan et al. |
| 2010/0122907 A1 | 5/2010 | Stanford et al. |
| 2010/0148126 A1 | 6/2010 | Guan et al. |
| 2010/0243449 A1 | 9/2010 | Oliver |
| 2010/0261247 A1 | 10/2010 | Hanzel et al. |
| 2010/0292101 A1 | 11/2010 | So |
| 2010/0297644 A1 | 11/2010 | Kokoris et al. |
| 2010/0301398 A1 | 12/2010 | Rothberg et al. |
| 2010/0320094 A1 | 12/2010 | White et al. |
| 2010/0331194 A1 | 12/2010 | Turner et al. |
| 2011/0005918 A1 | 1/2011 | Akeson et al. |
| 2011/0014601 A2 | 1/2011 | Carroll et al. |
| 2011/0014611 A1 | 1/2011 | Ju et al. |
| 2011/0039259 A1 | 2/2011 | Ju et al. |
| 2011/0053284 A1 | 3/2011 | Meller et al. |
| 2011/0059505 A1 | 3/2011 | Hanzel et al. |
| 2011/0160093 A1 | 6/2011 | Van Den Boom et al. |
| 2011/0165652 A1 | 7/2011 | Hardin et al. |
| 2011/0168968 A1 | 7/2011 | Yang et al. |
| 2011/0174625 A1 | 7/2011 | Akeson et al. |
| 2011/0189659 A1 | 8/2011 | Clark et al. |
| 2011/0192723 A1 | 8/2011 | Chen et al. |
| 2011/0193249 A1 | 8/2011 | Chen et al. |
| 2011/0193570 A1 | 8/2011 | Chen et al. |
| 2011/0218414 A1 | 9/2011 | Kamath et al. |
| 2011/0226623 A1* | 9/2011 | Timp et al. .................. 204/543 |
| 2011/0244447 A1 | 10/2011 | Korlach |
| 2011/0287414 A1 | 11/2011 | Chen et al. |
| 2012/0034602 A1 | 2/2012 | Emig et al. |
| 2012/0040869 A1 | 2/2012 | Meller et al. |
| 2012/0052188 A1 | 3/2012 | Chen et al. |
| 2012/0094278 A1 | 4/2012 | Akeson et al. |
| 2012/0094332 A1 | 4/2012 | Lee et al. |
| 2012/0115736 A1 | 5/2012 | Bjornson et al. |
| 2012/0142006 A1 | 6/2012 | Ju et al. |
| 2012/0149021 A1 | 6/2012 | Yung et al. |
| 2012/0156680 A1 | 6/2012 | Ju et al. |
| 2012/0160681 A1 | 6/2012 | Davis et al. |

(56) References Cited

U.S. PATENT DOCUMENTS

| | | | |
|---|---|---|---|
| 2012/0160687 A1 | 6/2012 | Akeson et al. |
| 2012/0187963 A1 | 7/2012 | Chen |
| 2012/0188092 A1 | 7/2012 | Chen |
| 2012/0196759 A1 | 8/2012 | Chen |
| 2012/0261261 A1 | 10/2012 | Huber |
| 2013/0015068 A1 | 1/2013 | Chen et al. |
| 2013/0207205 A1 | 8/2013 | Chen |
| 2013/0237460 A1 | 9/2013 | Deierling et al. |
| 2013/0240359 A1 | 9/2013 | Turner et al. |
| 2013/0244340 A1 | 9/2013 | Davis et al. |
| 2013/0263946 A1 | 10/2013 | Afzali-Ardakani et al. |
| 2013/0264207 A1 | 10/2013 | Ju et al. |
| 2013/0280700 A1 | 10/2013 | Ju et al. |
| 2014/0014513 A1 | 1/2014 | Chen et al. |
| 2014/0034497 A1 | 2/2014 | Davis et al. |
| 2014/0093869 A1 | 4/2014 | Ju et al. |
| 2014/0134616 A1 | 5/2014 | Davis et al. |

FOREIGN PATENT DOCUMENTS

| | | |
|---|---|---|
| WO | WO 97/32999 A1 | 9/1997 |
| WO | WO 97/46704 A1 | 12/1997 |
| WO | WO 01/48235 A2 | 7/2001 |
| WO | WO 02/22883 A1 | 3/2002 |
| WO | WO 02/29003 A2 | 4/2002 |
| WO | WO 02/029003 A3 | 7/2002 |
| WO | WO 02/079519 A1 | 10/2002 |
| WO | WO 03/020734 A2 | 3/2003 |
| WO | WO 2004/007773 A1 | 1/2004 |
| WO | WO 2004/055160 A2 | 7/2004 |
| WO | WO 2004/055160 A3 | 8/2004 |
| WO | WO 2004/071155 A2 | 8/2004 |
| WO | WO 2004/072238 A2 | 8/2004 |
| WO | WO 2005/084367 A2 | 9/2005 |
| WO | WO 2005/084367 A3 | 12/2005 |
| WO | WO 2006/020775 A2 | 2/2006 |
| WO | WO 2007/002204 A2 | 1/2007 |
| WO | WO 2007/053702 A2 | 5/2007 |
| WO | WO 2007/053719 A2 | 5/2007 |
| WO | WO 2007/062105 A2 | 5/2007 |
| WO | WO 2007/127327 A2 | 11/2007 |
| WO | WO 2007/146158 A1 | 12/2007 |
| WO | WO 2007/053702 A3 | 1/2008 |
| WO | WO 2008/034602 A2 | 3/2008 |
| WO | WO 2008/069973 A2 | 6/2008 |
| WO | WO 2008/102120 A1 | 8/2008 |
| WO | WO 2008/124107 A1 | 10/2008 |
| WO | WO 2008/069973 A3 | 12/2008 |
| WO | WO 2008/034602 A3 | 2/2009 |
| WO | WO 2009/020682 A2 | 2/2009 |
| WO | WO 2007/002204 A3 | 4/2009 |
| WO | WO 2007/053719 A3 | 4/2009 |
| WO | WO 2007/062105 A3 | 4/2009 |
| WO | WO 2009/051807 A1 | 4/2009 |
| WO | WO 2009/054922 A1 | 4/2009 |
| WO | WO 2010/109197 A2 | 9/2010 |
| WO | WO 2011/038241 A1 | 3/2011 |
| WO | WO 2011/067559 A1 | 6/2011 |
| WO | WO 2011/097028 A1 | 8/2011 |
| WO | WO 2011/106459 A2 | 9/2011 |
| WO | WO 2012/009578 A2 | 1/2012 |
| WO | WO 2012/088339 A2 | 6/2012 |
| WO | WO 2012/088341 A2 | 6/2012 |
| WO | WO 2012/121756 A1 | 9/2012 |
| WO | WO 2013/109970 A1 | 7/2013 |
| WO | WO 2013/154999 A2 | 10/2013 |
| WO | WO 2013/191793 A1 | 12/2013 |

OTHER PUBLICATIONS

Singh, et al. Synthesis of natural flutimide and analogues fully substituted pyrazine-2,6-diones, endonuclease inhibitors of influenza virus. J Org Chem. Aug. 10, 2001;66(16):5504-16.
Smith, et al. Overstretching B-DNA: the elastic response of individual double-stranded and single-stranded DNA molecules. Science. Feb. 9, 1996;271(5250):795-9.
Streater, et al. Novel 3-hydroxy-2(1H)-pyridinones. Synthesis, iron(III)-chelating properties, and biological activity. J Med Chem. Jun. 1990;33(6):1749-55.
U.S. Appl. No. 13/745,688, filed Jan. 18, 2013, Davis et al.
Office action dated Apr. 11, 2013 for U.S. Appl. No. 12/658,603.
U.S. Appl. No. 13/396,522, filed Feb. 14, 2012, Chen.
Akeson, et al. Microsecond time-scale discrimination among polycytidylic acid, polyadenylic acid, and polyuridylic acid as homopolymers or as segments within single RNA molecules. Biophys J. Dec. 1999;77(6):3227-33.
Aksimentiev, et al. Microscopic Kinetics of DNA Translocation through synthetic nanopores. Biophys J. Sep. 2004;87(3):2086-97.
Andersen. Sequencing and the single channel. Biophys J. Dec. 1999;77(6):2899-901.
Ashkenasy, et al. Recognizing a single base in an individual DNA strand: a step toward DNA sequencing in nanopores. Angew Chem Int Ed Engl. Feb. 18, 2005;44(9):1401-4.
Atanasov, et al. Membrane on a chip: a functional tethered lipid bilayer membrane on silicon oxide surfaces. Biophys J. Sep. 2005;89(3):1780-8.
Baaken, et al. Planar microelectrode-cavity array for high-resolution and parallel electrical recording of membrane ionic currents. Lab Chip. Jun. 2008;8(6):938-44. Epub Apr. 16, 2008.
Bai, et al. Design and synthesis of a photocleavable biotinylated nucleotide for DNA analysis by mass spectrometry. Nucleic Acids Res. Jan. 26, 2004;32(2):535-41. Print 2004.
Benner, et al. Sequence-specific detection of individual DNA polymerase complexes in real time using a nanopore. Nat Nanotechnol. Nov. 2007;2(11):718-24. Epub Oct. 28, 2007.
Boireau, et al. Unique supramolecular assembly of a redox protein with nucleic acids onto hybrid bilayer: towards a dynamic DNA chip. Biosens Bioelectron. Feb. 15, 2005;20(8):1631-7.
Bokhari, et al. A parallel graph decomposition algorithm for DNA sequencing with nanopores. Bioinformatics. Apr. 1, 2005;21(7):889-96. Epub Nov. 11, 2004.
Buchmann, et al. Electrochemical release from gold-thiolate electrodes for controlled insertion of ion channels into bilayer membranes. Bioorg Med Chem. Mar. 15, 2004;12(6):1315-24.
Butler, et al. Ionic current blockades from DNA and RNA molecules in the alpha-hemolysin nanopore. Biophys J. Nov. 1, 2007;93(9):3229-40. Epub Aug. 3, 2007.
Butler, et al. of RNA orientation during translocation through a biological nanopore. Biophys J. Jan. 1, 2006;90(1):190-9. Epub Oct. 7, 2005.
Butler, et al. Single-molecule DNA detection with an engineered MspA protein nanopore. Proc Natl Acad Sci U S A. Dec. 30, 2008;105(52):20647-52. Epub Dec. 19, 2008.
Clarke, et al. Continuous base identification for single-molecule nanopore DNA sequencing. Nat Nanotechnol. Apr. 2009;4(4):265-70. Epub Feb. 22, 2009.
Cockroft, et al. A single-molecule nanopore device detects DNA polymerase activity with single-nucleotide resolution. J Am Chem Soc. Jan. 23, 2008;130(3):818-20. Epub Jan. 1, 2008.
Danelon, et al. Cell membranes suspended across nanoaperture arrays. Langmuir. Jan. 3, 2006;22(1):22-5.
Deamer, et al. Characterization of nucleic acids by nanopore analysis. Acc Chem Res. Oct. 2002;35(10):817-25.
Derrington, et al. Nanopore DNA sequencing with MspA. Proc Natl Acad Sci U S A. Sep. 14, 2010;107(37):16060-5. Epub Aug. 26, 2010.
Ervin, et al. Simultaneous alternating and direct current readout of protein ion channel blocking events using glass nanopore membranes. Anal Chem. Mar. 15, 2008;80(6):2069-76. Epub Feb. 23, 2008.
Flusberg, et al. Direct detection of DNA methylation during single-molecule, real-time sequencing. Nat Methods. Jun. 2010;7(6):461-5. Epub May 9, 2010.
Fologea, et al. Detecting single stranded DNA with a solid state nanopore. Nano Lett. Oct. 2005;5(10):1905-9.
Fologea, et al. Slowing DNA translocation in a solid-state nanopore. Nano Lett. Sep. 2005;5(9):1734-7.
Harlepp, et al. Probing complex RNA structures by mechanical force. Eur Phys J E Soft Matter. Dec. 2003;12(4):605-15.

(56) References Cited

OTHER PUBLICATIONS

Heng, et al. Stretching DNA using the electric field in a synthetic nanopore. Nano Lett. Oct. 2005;5(10):1883-8.
Heng, et al. The electromechanics of DNA in a synthetic nanopore. Biophys J. Feb. 1, 2006;90(3):1098-106. Epub Nov. 11, 2005.
Holden, et al. Direct introduction of single protein channels and pores into lipid bilayers. J Am Chem Soc. May 11, 2005;127(18):6502-3.
Holden, et al. Direct transfer of membrane proteins from bacteria to planar bilayers for rapid screening by single-channel recording. Nat Chem Biol. Jun. 2006;2(6):314-8. Epub May 7, 2006.
Hromada, et al. Single molecule measurements within individual membrane-bound ion channels using a polymer-based bilayer lipid membrane chip. Lab Chip. Apr. 2008;8(4):602-8. Epub Feb. 29, 2008.
International Preliminary Report on Patentability issued Dec. 24, 2008 in connection with International Application No. PCT/US2007/013559.
International search report and written opinion dated May 3, 2012 for PCT/US2012/020827.
International search report and written opinion dated Aug. 28, 2012 for PCT/US2011/066627.
International search report and written opinion dated Aug. 28, 2012 for PCT/US2011/066632.
International search report and written opinion dated Oct. 29, 2007 for PCT/US2007/013559.
International search report and written opinion dated Nov. 5, 2012 for PCT/US2011/064490.
Ju, et al. Cassette labeling for facile construction of energy transfer fluorescent primers. Nucleic Acids Res. Mar. 15, 1996;24(6):1144-8.
Ju, et al. Fluorescence energy transfer dye-labeled primers for DNA sequencing and analysis. Proc Natl Acad Sci U S A. May 9, 1995;92(10):4347-51.
Ju, et al. Four-color DNA sequencing by synthesis using cleavable fluorescent nucleotide reversible terminators. Proc Natl Acad Sci U S A. Dec. 26, 2006;103(52):19635-40. Epub Dec. 14, 2006.
Jurak, et al. Wettability and topography of phospholipid DPPC multilayers deposited by spin-coating on glass, silicon, and mica slides. Langmuir. Sep. 25, 2007;23(20):10156-63. Epub Aug. 28, 2007.
Kang, et al. A storable encapsulated bilayer chip containing a single protein nanopore. J Am Chem Soc. Apr. 18, 2007;129(15):4701-5. Epub Mar. 22, 2007.
Kasianowicz, et al. Characterization of individual polynucleotide molecules using a membrane channel. Proc Natl Acad Sci U S A. Nov. 26, 1996;93(24):13770-3.
Kasianowicz. Nanopores: flossing with DNA. Nat Mater. Jun. 2004;3(6):355-6.
Kawano, et al. Controlling the translocation of single-stranded DNA through alpha-hemolysin ion channels using viscosity. Langmuir. Jan. 20, 2009;25(2):1233-7.
Kumar, et al. PEG-labeled nucleotides and nanopore detection for single molecule DNA sequencing by synthesis. Sci Rep. 2012;2:684. Epub Sep. 21, 2012.
Kutik, et al. Dissecting membrane insertion of mitochondrial beta-barrel proteins. Cell. Mar. 21, 2008;132(6):1011-24.
Lee, et al. Enhancing the catalytic repertoire of nucleic acids: a systematic study of linker length and rigidity. Nucleic Acids Res. Apr. 1, 2001;29(7):1565-73.
Li, et al. A photocleavable fluorescent nucleotide for DNA sequencing and analysis. Proc Natl Acad Sci U S A. Jan. 21, 2003;100(2):414-9. Epub Jan. 6, 2003.
Linear Technology, High Efficiency Thermoelectric Cooler Controller, 2001.
Low Noise, Dual Switched Integrator, Burr-Brown Corporation, Sep. 1994.
Madampage, et al. Nanopore detection of antibody prion interactions. Anal Biochem. Jan. 1, 2010;396(1):36-41. Epub Aug. 21, 2009.
Mathe, et al. Nanopore unzipping of individual DNA hairpin molecules. Biophys J. Nov. 2004;87(5):3205-12. Epub Sep. 3, 2004.
Maurer, et al. Reconstitution of ion channels in agarose-supported silicon orifices. Biosens Bioelectron. May 15, 2007;22(11):2577-84. Epub Nov. 13, 2006.
McNally, et al. Optical recognition of converted DNA nucleotides for single-molecule DNA sequencing using nanopore arrays. Nano Lett. Jun. 9, 2010;10(6):2237-44.
Meller, et al. Rapid nanopore discrimination between single polynucleotide molecules. Proc Natl Acad Sci U S A. Feb. 1, 2000;97(3):1079-84.
Meller, et al. Single molecule measurements of DNA transport through a nanopore. Electrophoresis. Aug. 2002;23(16):2583-91.
Mohammad, et al. Controlling a single protein in a nanopore through electrostatic traps. J Am Chem Soc. Mar. 26, 2008;130(12):4081-8. Epub Mar. 6, 2008.
Nakane, et al. A Nanosensor for Transmembrane Capture and Identification of Single Nucleic Acid Molecules, Biophysical Journal, vol. 87, Issue 1, Jul. 2004, pp. 615-621, ISSN 0006-3495.
Office action dated Apr. 26, 2012 for U.S. Appl. No. 12/658,591.
Office action dated Apr. 26, 2012 for U.S. Appl. No. 12/658,601.
Office action dated Jun. 15, 2012 for U.S. Appl. No. 12/658,604.
Office action dated Jun. 28, 2012 for U.S. Appl. No. 12/308,091.
Office action dated Aug. 3, 2012 for U.S. Appl. No. 12/658,602.
Office action dated Oct. 2, 2012 for U.S. Appl. No. 12/658,603.
Office action dated Oct. 16, 2012 for U.S. Appl. No. 12/658,601.
Office action dated Oct. 25, 2012 for U.S. Appl. No. 12/658,591.
Oxford Nanopore Technologies, Sensor Array Chip, Jul. 14, 2011.
Park, et al. DNA hybridization sensors based on electrochemical impedance spectroscopy as a detection tool. Sensors (Basel). 2009;9(12):9513-32. Epub Nov. 26, 2009.
Pourmand, et al. Multiplex Pyrosequencing. Acids Res. Apr. 1, 2002;30(7):e31.
Purnell, et al. Discrimination of single base substitutions in a DNA strand immobilized in a biological nanopore. ACS Nano. Sep. 22, 2009;3(9):2533-8.
Rosenblum, et al. New dye-labeled terminators for improved DNA sequencing patterns. Nucleic Acids Res. Nov. 15, 1997;25(22):4500-4.
Rostovtsev, et al. A stepwise huisgen cycloaddition process: copper(I)-catalyzed regioselective "ligation" of azides and terminal alkynes. Angew Chem Int Ed Engl. Jul. 15, 2002;41(14):2596-9.
Rotem et al., Temperature Measurement in the Intel Core Duo Processor, 2007.
Sanchez-Magraner, et al. Membrane insertion of *Escherichia coli* alpha-hemolysin is independent from membrane lysis. J Biol Chem. Mar. 3, 2006;281(9):5461-7. Epub Dec. 22, 2005.
Sauer-Budge, et al. Unzipping kinetics of double-stranded DNA in a nanopore. Phys Rev Lett. Jun. 13, 2003;90(23):238101. Epub Jun. 9, 2003.
Seo, et al. Photocleavable fluorescent nucleotides for DNA sequencing on a chip constructed by site-specific coupling chemistry. Proc Natl Acad Sci U S A. Apr. 13, 2004;101(15):5488-93. Epub Apr. 2, 2004.
Shim, et al. Encapsulating a single G-quadruplex aptamer in a protein nanocavity. J Phys Chem B. Jul. 17, 2008;112(28):8354-60. Epub Jun. 19, 2008.
Simon, et al. Formation and stability of a suspended biomimetic lipid bilayer on silicon submicrometer-sized pores. J Colloid Interface Sci. Apr. 15, 2007;308(2):337-43. Epub Jan. 31, 2007.
Singer et al., Nanopore Based Sequence Specific Detection of Duplex DNA for Genomic Profiling, Jan. 8, 2010, published Jan. 20, 2010, pp. 738-742.
Stefureac, et al. Nanopore analysis of the interaction of metal ions with prion proteins and peptides. Biochem Cell Biol. Apr. 2010;88(2):347-58.
Stefureac, et al. Transport of alpha-helical peptides through alpha-hemolysin and aerolysin pores. Biochemistry. Aug. 1, 2006;45(30):9172-9.
Stoddart, et al. Nucleobase recognition in ssDNA at the central constriction of the alpha-hemolysin pore. Nano Lett. Sep. 8, 2010;10(9):3633-7.
Studer, et al. Formation of individual protein channels in lipid bilayers suspended in nanopores. Colloids Surf B Biointerfaces. Oct. 15, 2009;73(2):325-31. Epub Jun. 10, 2009.

(56) References Cited

OTHER PUBLICATIONS

Suzuki, et al. Highly reproducible method of planar lipid bilayer reconstitution in polymethyl methacrylate microfluidic chip. Langmuir. Feb. 14, 2006;22(4):1937-42.

Thomson et al. Preliminary nanopore cheminformatics analysis of aptamer-target binding strength. BMC Bioinformatics. Nov. 1, 2007;8 Suppl 7:S11.

Vercoutere, et al. Discrimination among individual Watson-Crick base pairs at the termini of single DNA hairpin molecules. Nucleic Acids Res. Feb. 15, 2003;31(4):1311-8.

Vercoutere, et al. Rapid discrimination among individual DNA hairpin molecules at single-nucleotide resolution using an ion channel. Nat Biotechnol. Mar. 2001;19(3):248-52.

Viasnoff, et al. Probing DNA base pairing energy profiles using a nanopore. Eur Biophys J. Feb. 2009;38(2):263-9. Epub Oct. 3, 2008.

Wang, et al. DNA heterogeneity and phosphorylation unveiled by single-molecule electrophoresis. Proc Natl Acad Sci U S A. Sep. 14, 2004;101(37):13472-7. Epub Sep. 1, 2004.

Wanunu, et al. DNA profiling using solid-state nanopores: detection of DNA-binding molecules. Nano Lett. Oct. 2009;9(10):3498-502.

Weng, et al. Fluid biomembranes supported on nanoporous aerogel/xerogel substrates. Langmuir. Aug. 17, 2004;20(17):7232-9.

Wilson, et al. Electronic control of DNA polymerase binding and unbinding to single DNA molecules. ACS Nano. Apr. 28, 2009;3(4):995-1003.

Wilson, et al. Feedback control of a DNA molecule tethered in a nanopore to repeatedly probe DNA-binding enzymes. Conf Proc IEEE Eng Med Biol Soc. 2008;2008:5745-8.

Winters-Hilt, et al. Nanopore-based kinetics analysis of individual antibody-channel and antibody-antigen interactions. BMC Bioinformatics. Nov. 1, 2007;8 Suppl 7:S20.

Woodside, et al. Direct measurement of the full, sequence-dependent folding landscape of a nucleic acid. Science. Nov. 10, 2006;314(5801):1001-4.

Woodside, et al. Nanomechanical measurements of the sequence-dependent folding landscapes of single nucleic acid hairpins. Proc Natl Acad Sci U S A. Apr. 18, 2006;103(16):6190-5. Epub Apr. 10, 2006.

Wu, et al. Single-molecule detection of nitrogen mustards by covalent reaction within a protein nanopore. J Am Chem Soc. May 28, 2008;130(21):6813-9. Epub Apr. 30, 2008.

Zeineldin, et al. Using bicellar mixtures to form supported and suspended lipid bilayers on silicon chips. Langmuir. Sep. 12, 2006;22(19):8163-8.

Zwolak, et al. Electronic signature of DNA nucleotides via transverse transport. Nano Lett. Mar. 2005;5(3):421-4.

U.S. Appl. No. 14/073,445, filed Nov. 6, 2013, Davis et al.

Chinese office action dated Jul. 2, 2012 for CN Application No. 200780028545.1.

Chinese office action dated Oct. 12, 2013 for CN Application No. 200780028545.1.

International search report and written opinion dated Sep. 13, 2013 for PCT Application No. US2013/046012.

International search report dated Feb. 26, 2013 for PCT Application No. US2012/069911.

McGuigan, et al. DNA fingerprinting by sampled sequencing. Methods in Enzymology. 1993; 218:241-258.

Office action dated Jan. 17, 2014 for U.S. Appl. No. 13/276,200.

Rosenstein, et al. Integrated nanopore sensing platform with submicrosecond temporal resolution. Nat Methods. Mar. 18, 2012;9(5):487-92. doi: 10.1038/nmeth.1932.

Venkatesan, et al. Nanopore sensors for nucleic acid analysis. Nat Nanotechnol. Sep. 18, 2011;6(10):615-24. doi: 10.1038/nnano.2011.129.

Bezrukov, et al. Counting polymers moving through a single ion channel. Nature. Jul. 28, 1994;370(6487):279-81.

Bezrukov, et al. Dynamic partitioning of neutral polymers into a single ion channel. In NATO Advanced Research Workshop: Structure and dynamics of confined polymers. Kulwer Press. 2002; 117-130.

Bezrukov, et al. Dynamics and free energy of polymers partitioning into a nanoscale pore. Macromolecules. 1996; 29:8517-8522.

Churbanov, et al. Duration learning for analysis of nanopore ionic current blockades. BMC Bioinformatics. Nov. 1, 2007;8 Suppl 7:S14.

Einstein. Investigations on the theory of Brownian movement. Dover, New York. 1956, Table of Contents only.

Gu, et al. Stochastic sensing of organic analytes by a pore-forming protein containing a molecular adapter. Nature. Apr. 22, 1999;398(6729):686-90.

Haas, et al. Improvement of the quality of self assembled bilayer lipid membrances by using a negative potential. Bioelectrochemistry. Aug. 2001;54(1):1-10.

Halverson, et al. Asymmetric blockade of anthrax protective antigen ion channel asymmetric blockade. J Biol Chem. Oct. 7, 2005; 280(40):34056-62. Epub Aug. 8, 2005.

Heins, et al. Detecting single porphyrin molecules in a conically shaped synthetic nanopore. Nano Lett. Sep. 2005;5(9):1824-9.

Ito, et al. Simultaneous determination of the size and surface charge of individual nanoparticles using a carbon nanotube-based Coulter counter. Anal Chem. May 15, 2003;75(10):2399-406.

Kasianowicz, et al. Physics of DNA threading through a nanometer pore and applications to simultaneous multianalyte sesnsing. In NATO Advanced Research Workshop: Structure and dynamics of confined polymers. Kluwer Press. 2002; 141-163.

Kasianowicz, et al. Simultaneous multianalysis detection with a nanopore. Anal. Chem. 2001; 73:2268-2272.

Krasilnikov, et al. A simple method for the determination of the pore radius of ion channels in planar lipid bilayer membranes. FEMS Microbiol Immunol. Sep. 1992;5(1-3):93-100.

Krasilnikov, et al. Single polymer molecules in a protein nanopore in the limit of a strong polymer-pore attraction. Phys Rev Lett. 2006; 97(1):018301. Epub Jul. 5, 2006.

Krasilnikov, et al. Sizing channels with neutral polymers. In NATO Advanced Research Workshop: Structure and dynamics of confined polymers. Kluwer Press. 2002; 97-116.

Kullman, et al. Transport of maltodextrins through maltoporin: a single-channel study. Biophys J. Feb. 2002;82(2):803-12.

Mathe, et al. Orientation discrimination of single-stranded DNA inside the alpha-hemolysin membrane channel. Proc Natl Acad Sci U S A. Aug. 30, 2005;102(35):12377-82. Epub Aug. 19, 2005.

Movileanu, et al. Partitioning of a polymer into a nanoscopic protein pore obeys a simple scaling law. Proc Natl Acad Sci U S A. Aug. 28, 2001;98(18):10137-41. Epub Aug. 14, 2001.

Movileanu, et al. Partitioning of individual flexible polymers into a nanoscopic protein pore. Biophys J. Aug. 2003;85(2):897-910.

Reiner, et al. Temperature sculpting in yoctoliter volumes. J Am Chem Soc. Feb. 27, 2013;135(8):3087-94. doi: 10.1021/ja309892e. Epub Feb. 14, 2013.

Reiner, et al. Theory for polymer analysis using nanopore-based single-molecule mass spectrometry. Proc Natl Acad Sci U S A. Jul. 6, 2010;107(27):12080-5. doi: 10.1073/Pnas.1002194107. Epub Jun. 21, 2010.

Robertson, et al. Single-molecule mass spectrometry in solution using a solitary nanopore. Proc Natl Acad Sci U S A. 2007;104(20):8207-11. Epub May 9, 2007.

Saleh, et al. Direct detection of antibody-antigen binding using an on-chip artificial pore. Proc Natl Acad Sci U S A. Feb. 4, 2003;100(3):820-4. Epub Jan. 27, 2003.

Stanford, et al. Transport of DNA through a single nanometer-scale pore: evolution of signal structure. IEEE Workshop on Genomic Signal Processing and Statistics. Baltimore, MD. May 26, 2004.

Stanford, et al. Using HMMs to Quantify Signals from DNA Driven Through a Nanometer-Scale Pore. IEEE Workshop on Genomic Signal Processing and Statistics. Raleigh, NC. Oct. 2002; 11-13.

Storm, et al. Translocation of double-strand DNA through a silicon oxide nanopore. Phys Rev E Stat Nonlin Soft Matter Phys. May 2005;71(5 Pt 1):051903. Epub May 6, 2005.

Allowed claims dated Apr. 30, 2008 in U.S. Appl. No. 12/084,457.

Chinese office action dated Apr. 9, 2013 for CN Application No. 200780028545.1. (with English translation).

(56) References Cited

OTHER PUBLICATIONS

Eid, et al. Real-time DNA sequencing from single polymerase molecules. Science. Jan. 2, 2009;323(5910):133-8. doi: 10.1126/science.1162986. Epub Nov. 20, 2008.
European search report and opinion dated Apr. 16, 2014 for EP Application No. 11848220.7.
Guranowski, et al. Selective degradation of 2'-adenylated diadenosine tri- and tetraphosphates, Ap(3)A and Ap(4)A, by two specific human dinucleoside polyphosphate hydrolases. Arch Biochem Biophys. Jan. 1, 2000;373(1):218-24.
International search report and written opinion dated Oct. 25, 2013 for PCT Application No. US2013/035635.
Invitation to Pay Additional Fees dated Aug. 19, 2013 for PCT Application No. US2013/035635.
Kumar, et al. Terminal phosphate labeled nucleotides: synthesis, applications, and linker effect on incorporation by DNA polymerases. Nucleosides Nucleotides Nucleic Acids. 2005;24(5-7):401-8.
Mulder, et al. Nucleotide modification at the gamma-phosphate leads to the improved fidelity of HIV-1 reverse transcriptase. Nucleic Acids Res. Sep. 1, 2005;33(15):4865-73. Print 2005.
Office Action dated Mar. 27, 2014 in connection with Chinese Patent Application No. 201180063978.7 (with English translation of cover page only).
Pending claims dated Jul. 19, 2011 in U.S. Appl. No. 13/186,353.
Pending claims dated Dec. 14, 2007 in U.S. Appl. No. 11/922,385.
Pending claims in U.S. Appl. No. 13/959,660, filed Aug. 5, 2013, Ju et al.
Reynolds, et al. Synthesis and stability of novel terminal phosphate-labeled nucleotides. Nucleosides Nucleotides Nucleic Acids. Jan. 2008;27(1):18-30. doi:10.1080/15257770701571768.
Sood, et al. Terminal phosphate-labeled nucleotides with improved substrate properties for homogeneous nucleic acid assays. J Am Chem Soc. Mar. 2, 2005;127(8):2394-5.
Office action dated Feb. 25, 2013 for U.S. Appl. No. 13/396,522.
International search report dated Feb. 7, 2014 for PCT Application No. US2013/068967.
International search report dated Sep. 24, 2013 for PCT Application No. US2013/035630.
Office action dated Mar. 28, 2014 for U.S. Appl. No. 13/333,932.
Office action dated Apr. 10, 2014 for U.S. Appl. No. 12/658,602.
Office action dated Apr. 10, 2014 for U.S. Appl. No. 13/759,701.
Office action dated Apr. 11, 2014 for U.S. Appl. No. 12/658,601.
Office action dated Apr. 15, 2014 for U.S. Appl. No. 12/658,591.
Schneider et al. DNA sequencing with nanopores. Nat Biotechnol. Apr. 10, 2012;30(4):326-8. doi: 10.1038/nbt.2181.
International search report and written opinion dated Mar. 18, 2013 for PCT/US2012/063099.
International search report and written opinion dated May 9, 2013 for PCT/US2013/028058.
Stoddart, et al. Single-nucleotide discrimination in immobilized DNA oligonucleotides with a biological nanopore. Proc Natl Acad Sci U S A. May 12, 2009;106(19):7702-7. doi: 10.1073/pnas.0901054106. Epub Apr. 20, 2009.
UK search and examination report dated Feb. 25, 2013 for GB Application No. 1216656.7.
UK search and examination report dated May 1, 2013 for GB Application No. 1216026.3.
Henrickson, et al. Probing single nanometer-scale pores with polymeric molecular rulers. J Chem Phys. Apr. 7, 2010;132(13):135101. doi: 10.1063/1.3328875.
International search report dated Feb. 4, 2013 for PCT/US2011/065640.
Office action dated Dec. 17, 2012 for U.S. Appl. No. 13/620,973.
U.S. Appl. No. 13/918,626, filed Jun. 14, 2013, Davis et al.
International search report and written opinion dated May 16, 2013 for PCT Application No. US2013/026514.
International search report and written opinion dated Jun. 2, 2013 for PCT Application No. US2013/022273.

* cited by examiner

A   Electrodes
B1  Treated Hydrophobic/Lipophillic Semiconductor Surface
B2  Semiconductor substrate containing electronic circuitry
C   Solvent/Lipid
D   Lipid Bilayer
E   Pore
F   Conductive solution (salt solution)
G   Chip Packaging
H   Peltier device for electronic temperature control

NANOPORE-BASED SINGLE MOLECULE CHARACTERIZATION

CROSS-REFERENCE TO RELATED APPLICATIONS

The present application claims priority to U.S. Provisional Application Nos. 61/426,322, filed Dec. 22, 2010; and 61/426,323, filed Dec. 22, 2010; which are incorporated herein by reference in their entireties.

FIELD OF THE INVENTION

The present invention relates to a method of DNA sequencing using nanopore detectors in the presence of speed bumps.

BACKGROUND OF THE INVENTION

A nanopore is a nanometer-scale pore providing the sole pathway for an ionic current. An exemplary nanopore can be created from depositing alpha hemolysin onto the surface of a lipid bilayer under electrical stimulus, as described in US Application Publication No. 2011/0193570, which are herein incorporated by reference in their entireties.

Nanopore sequencing has the potential to become a direct, fast, and inexpensive DNA sequencing technology. Ideally, individual nucleotides of a single-stranded (ss) DNA passing through a nanopore will uniquely modulate an ionic current flowing through the nanopore, allowing the record of the current to provide DNA sequence information. However, a common challenge to nanopore sequencing is that the ss DNA translocation is rapid, and the electrical signals obtained cannot be resolved for reliable DNA sequencing. DNA duplex sections have been used to slow translocation of a ss DNA to provide more resolvable electrical signals. However, as the currently available methods conduct nanopore detection at about room temperature or higher, a relatively long DNA duplex section is required to stall the ss DNA in the nanopore.

Thus, there is a need to provide a method to sequence an unknown DNA using nanopore technology.

SUMMARY OF THE INVENTION

One aspect of the invention relates to characterization and identification of an unknown DNA using a nanopore detector facilitated by a random speed bump pool.

Another aspect of the invention relates to detection and/or identification of one or more known structure in a test DNA using nanopore detector facilitated by one or more speed bumps.

Another aspect of the invention relates to characterization and/or identification of an unknown DNA in a test DNA using nanopore detector facilitated by one or more speed bumps.

DETAILED DESCRIPTION OF THE INVENTION

Definitions

Figure 1:
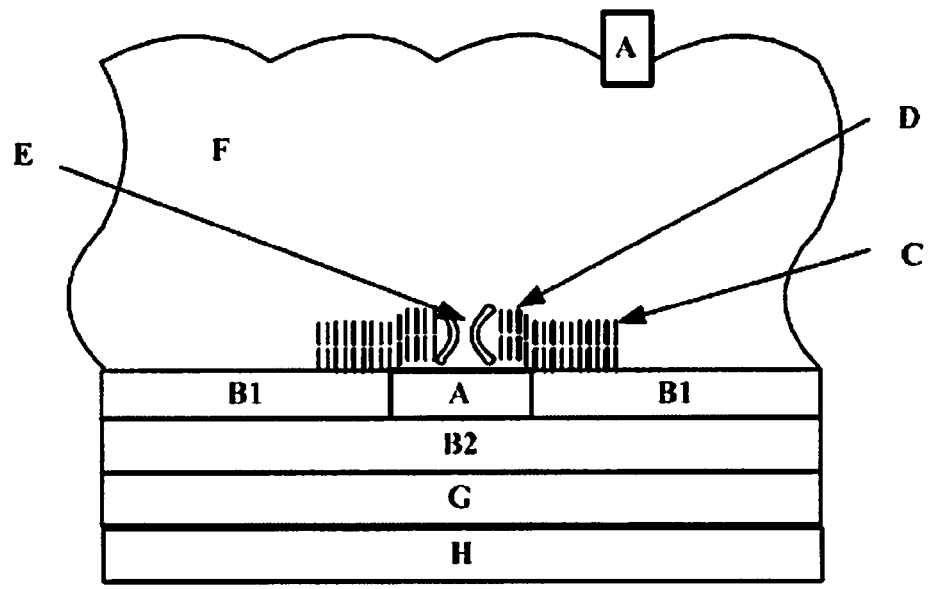
FIG. 1 illustrates an example of a nanopore detector.

A test DNA, as used herein, is a DNA molecule that passes through a nanopore for detection purposes. A test DNA can be a single-stranded test DNA (ss test DNA) and a double-stranded test DNA (ds test DNA). A ss test DNA, as used herein, comprises a section of ss DNA that is to be bound by a speed bump in a method described herein. A ss test DNA may further comprise an unknown DNA and other functional moieties (e.g. pre-bulky structure, identifiers and isolation tags).

A pre-bulky structure, as used herein, is an oligonucleotide structure in a DNA molecule which can form a bulky structure under certain conditions. The pre-bulky structure can be a ss DNA or a ds DNA.

A bulky structure, as used herein, is nucleotide structure formed from a pre-bulky structure in a ss test DNA molecule. The bulky structure stalls the test DNA molecule in a nanopore at a working condition until the working condition is changed to another condition wherein the bulky structure is converted to the pre-bulky structure or other structures that cannot stall the test DNA molecule any more. Examples of bulky structures include, without limitation, 2-D and 3-D structures such as DNA duplex structures, DNA hairpin structures, multi-hairpin structures and multi-arm structures.

A nanopore, as used herein, is a pore of nanometer dimensions formed by a pore-forming protein being inserted into a membrane. Typically, the membrane is an electrically insulating lipid bilayer membrane. Pore-forming proteins, such as alpha hemolysin and MspA porin, are inserted into the membrane to form nanopores through the protein molecule and the membrane. Electrophysiology measurements can be taken by measuring the ionic current passing through a nanopore as a voltage is applied across the membrane. A nanopore can be utilized as a molecule detector by monitoring the ionic current variation in response to the passage of the molecule through the nanopore. A nanopore can be a synthetic, man-made, biologically altered, wild-type biological nanopore, or a combination thereof.

A speed bump, as used herein, is an oligonucleotide molecule that forms a complex with a binding segment of a test DNA molecule. When the test DNA molecule goes through a nanopore under an electric potential, the complex formed between the speed bump and the binding segment stalls the test DNA molecule in the nanopore for a dwelling time long enough for the nanopore detector to obtain structure information of the test DNA molecule. After the dwelling time, the complex dissociates and the test DNA molecule moves forward through the nanopore.

An identifier, as used herein, is a known structure in a test DNA that can be detected or identified by the method described herein. Examples of identifiers include, without limitation, direction identifiers, reference signal identifiers, sample source identifiers, and sample identifiers. The identifiers may comprise one or more nucleotides or structures that provide distinctive electrical signals that are easily identified. Examples of such nucleotides and structures include, without limitation, isodG, isodC, methylated nucleotides, locked nucleic acids, universal nucleotides, and abasic nucleotides. In certain embodiments, an abasic nucleotide provides a stronger signal than a primary nucleotide. Thus, the electrical signal detected by a nanopore for a sequence comprising both abasic nucleotides and primary nucleotides will provide a signal more intense than the electrical signal obtained from primary nucleotide only sequences. For example, a 4~5 base sequence comprising about 25% abasic nucleotides may provide a signal more than twice as strong as a 4~5 base sequence comprising only primary nucleotides. The more abasic nucleotides the sequence have, the stronger electrical signal the sequence. Thus, identifiers may provide electrical signals of a desired intense (e.g. about twice, about 3, 4, 5, 6, 7, 8, 9, or about 10 times stronger than that of primary oligonucleotides having the same length) by changing the amount of abasic nucleotides in the identifier sequences.

Direction identifier, as used herein, is a known sequence positioned 0, 1, 2, 3, 4, 5, 6, 7, 8, 9, 10, 11, 12, 13, 14, 15, 16, 17, 18, 19, or 20 bases from a bulky structure formed from a pre-bulky structure. When the bulky structure is properly formed, it will stop the ss test DNA molecule from flowing through a nanopore that the ss test DNA molecule is in. Thus, when the bulky structure is stopped inside the nanopore, a set of electrical signals will be obtained, which provide sequence information of the sequence that is in front of the bulky structure and the first basepair of the bulky structure, in the flow direction of the ss test DNA molecule. When the sequence is known, such electrical signals can:
  1) verify that the pre-bulky structure has properly formed into the bulky structure such that the bulky structure stops the ss test DNA molecule from flowing through the nanopore;
  2) indicate that the ss test DNA molecule has reached one end of the single strand section of the ss test DNA, and
  3) serve as a reference or calibration read to base line other electrical signals obtained in the same nanopore.

In certain embodiments, the direction identifier comprises one or more nucleotides or structures that provide distinctive electrical signals that are easily identified. Examples of such nucleotides and structures include, without limitation, nucleotides comprising isodG or isodC, abasic nucleotides, methylated nucleotides, etc.

Reference signal identifier, as used herein, is a known sequence in a test DNA, when detected or identified by the method described herein, serves as a reference or calibration read to base line other electrical signals obtained in the same nanopore.

Sample source identifier, as used herein, is a known sequence in a test DNA, when detected or identified by the method described herein, is used to identify the source that the unknown DNA is from.

Sample identifier, as used herein, is a known sequence in a test DNA, when detected or identified by the method described herein, is used to identify the individual unknown DNA.

A known speed bump is a speed bump that specifically binds to a known sequence in a ss test DNA. Because the binding segment on the ss test DNA (the known sequence) is known, the speed bump structure can also be known (e.g. complementary to the known sequence on the ss test DNA).

A random speed bump pool, as used herein, comprises a collection of speed bumps that can bind to all sections of a test DNA molecule or a fragment thereof. An example of random speed bump pool comprises oligonucleotides having universal nucleobases which base-pair with all primary nucleobases (A, T, C and G). Another example of random speed bump pool comprises oligonucleotides of a given length having all possible combinations of primary nucleobases. Another example of random speed bump pool comprises oligonucleotides of a given length having every possible combination of primary nucleobases and universal nucleobases. Another example of random speed bump pool comprises speed bumps having universal nucleobases at designated positions and all combinations of primary nucleobases at the other positions. Another example of random speed bumps is a combination of ss speed bumps, which form duplex sections with ss test DNA, and the duplex sections have about the same melting temperatures. These ss speed bumps may have the same or different lengths, and/or the same or different nucleotides.

"About," as used herein, refers to +/−10% of the recited value.

The present invention is directed to a method for detecting and/or identifying a sequence in a test DNA using a nanopore detector. The DNA sequence is trapped in the nanopore by one or two bulky structures formed at the end(s) of the DNA sequence. Known speed bumps are used to bind to known sequences in the test DNA for the detection/identification of the known sequences. A random speed bump pool is used to bind to the test DNA or a fragment thereof in a random fashion. The nucleotides of the test DNA or the fragment thereof will be stalled in the nanopore by a known speed bump or a random speed bump for a time long enough to collect the nucleotide sequence information. The test DNA may further comprise known structures such as direction identifiers, reference signal identifiers, sample source identifiers, sample identifiers to provide information, e.g. formation of the bulky structures, source of the test DNA, and identification of the test DNA.

FIG. 1 shows an example of a nanopore detector having temperature control, which is prepared according to US Application Publication No. 2011/0193570. The nanopore detector comprises electrodes (A), a treated semiconductor hydrophobic surface (B1) in which is embedded a conductive electrode (A) that is connected to electrical circuitry in a semiconductor substrate (B2), a layer of lipid material (C) created over an electrode (A) and a small portion of the hydrophobic surface closeby (B1), and a nanopore (D) inserted in the lipid material through a conductive salt solution (F). A sample detected goes through the pore (E) in the nanopore. The semiconductor chip sensor is placed in package (G) and this, in turn, is in the vicinity of a Peltier device or temperature control element (H). Multiple nanopore detectors can be created to form a nanopore array.

Figure 2:
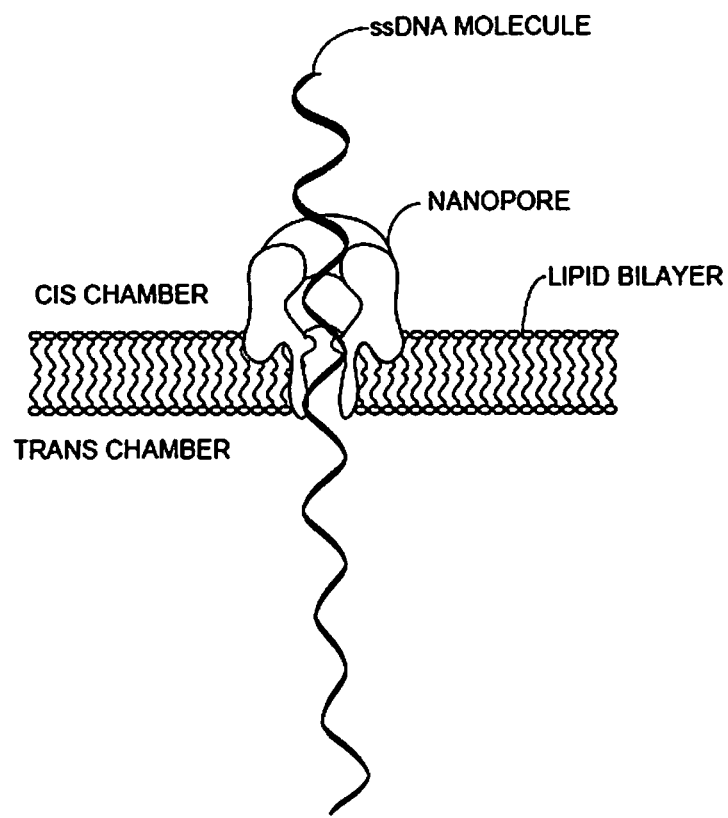
FIG. 2 illustrates the passage of a single stranded (ss) test DNA molecule through a nanopore.

As illustrated in FIG. 2, a single-stranded (ss) DNA molecule can go through a nanopore under an applied electric potential. A set of electrical signals corresponding to the brief blockages of ion flow through the nanopore by the ss DNA molecule is detected as the ss DNA molecule is threaded through the nanopore. In the absence of speed bumps or bulky structures, the ss DNA molecule encounters little resistance and travels through the nanopore too quickly for electrical signals to be reliably recorded for sequencing of the ss DNA.

Figure 3:
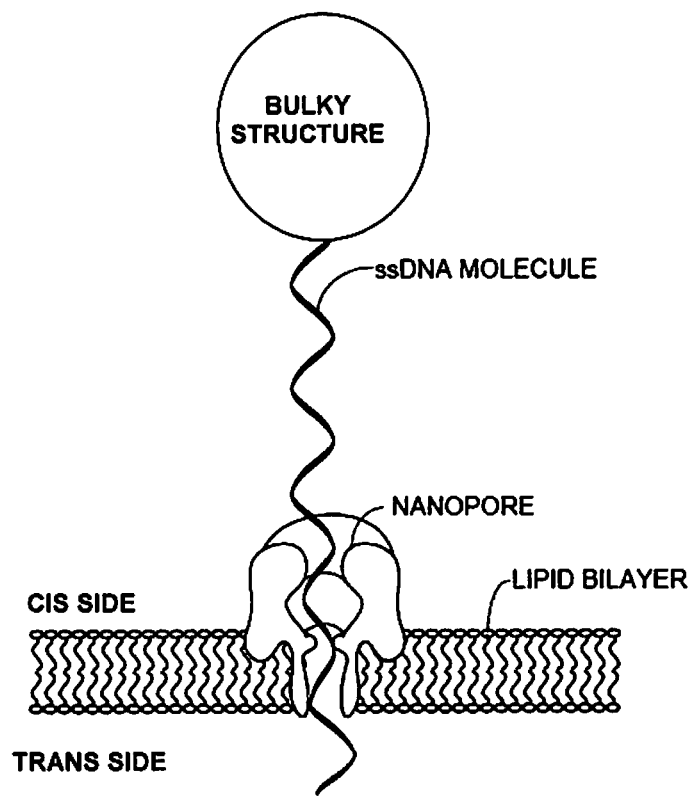
FIG. 3 illustrates a bulky structure formed at the trailing end of a ss test DNA molecule to stall the passage of the ss test DNA through a nanopore.

Bulky structures (BSs) have been used to stop the passage of a ss DNA through a nanopore. FIG. 3 illustrates a trailing end BS used to stop the passage of a ss DNA molecule through a nanopore. The BS can be a hairpin structure formed at one end of the ss DNA by wrapping the trailing end of the ss DNA upon itself. Typically, the ss DNA can be threaded through the nanopore under an applied electric potential until the bulky hairpin structure reaches the entrance of the nanopore. Since the hairpin structure is larger than the diameter of the nanopore, the ss DNA is stalled in the nanopore long enough to obtain a set of electrical signals of the ss DNA. However, the electrical signals obtained reflects the structure of only a portion of the DNA that is in front of the hairpin or in front of the specific duplex region and therefore in or near the constriction area of the nanopore.

Figure 4:
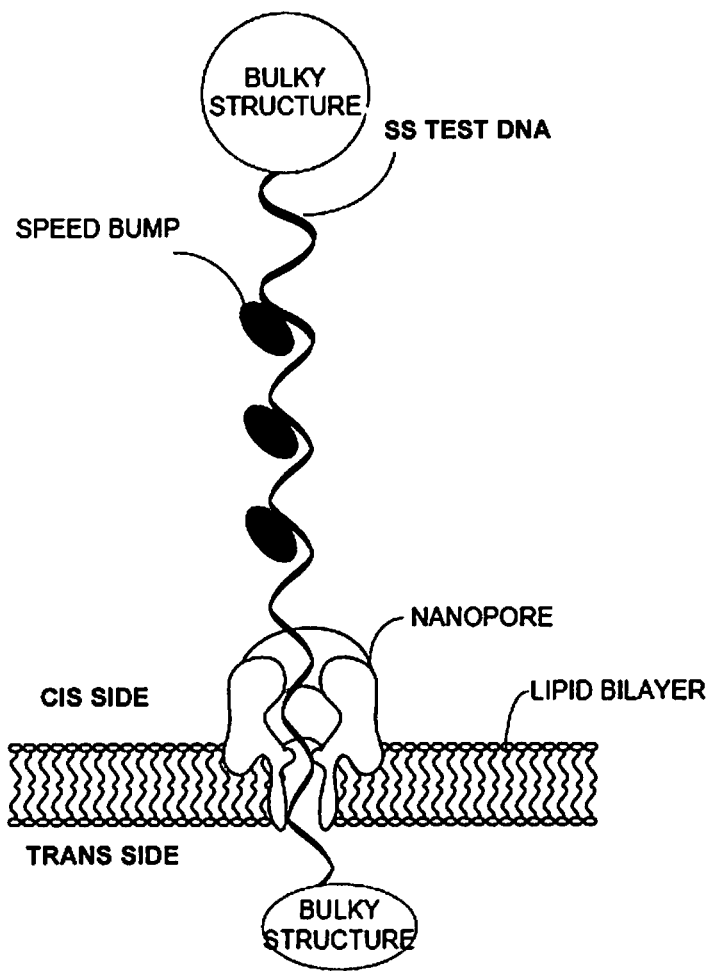
FIG. 4 illustrate multiple speed bumps bound to a ss test DNA molecule, wherein the ss test DNA is trapped in a nanopore by having bulky structures on both ends.

FIG. 4 illustrates a ss test DNA trapped in a nanopore by two bulky structures. The nanopore detection is carried out at a working temperature that may be lower than room temperature so that one or more shorter DNA duplex, sections can be formed between speed bumps and the ss test DNA (speed bump-test DNA duplex segments). The speed bump-test DNA duplex segment stalls the ss test DNA for a sufficient dwelling time to obtain sequence information of the ss test DNA segment in front of the speed bump-test DNA duplex segment and the first basepair of the speed bump-test DNA duplex segment in the flow direction of the ss test DNA. Then the speed bump-test DNA duplex segment dissociate and the ss test DNA moves forward through the nanopore until stalled by another speed bump-test DNA duplex segment or stopped by a BS on one end of the ss test DNA. Once the ss test DNA reaches one end, the electric potential can be optionally at a reduced value or at a reversed polarity to move the ss test DNA to a reversed direction and repeat the process as desired.

Figure 5:
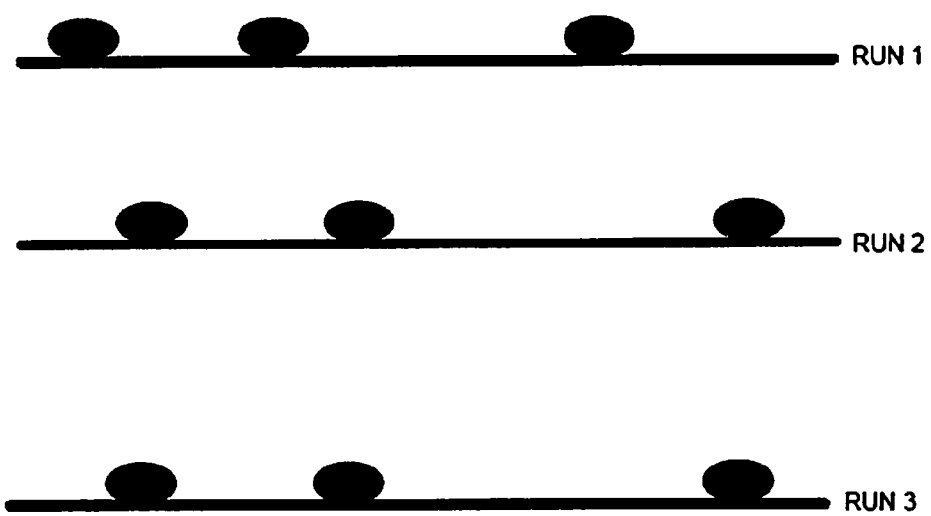
FIG. 5 illustrates different binding patterns achieved by contacting a ss test DNA with a random speed bump pool.
Figure 6:
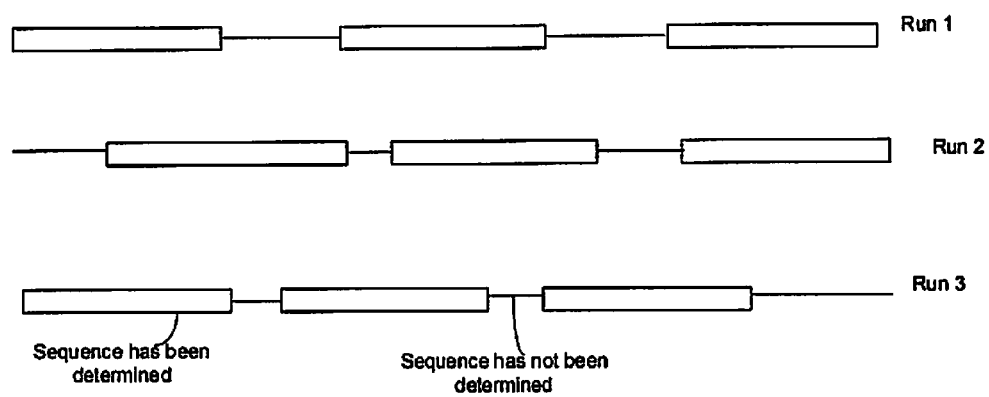
FIG. 6 illustrates different sequence information patterns achieved by randomly stalling a ss test DNA in a nanopore to obtain sequence information.

When the ss test DNA has an unknown sequence (or unknown DNA), a random speed bump pool can be constructed and bound to random sections of the ss test DNA. As every section of the ss test DNA can be bound by at least one speed bump in the random speed bump pool, the binding patterns achieved by contacting a ss test DNA with a random speed bump pool each time can be random (FIG. 5). Thus, the segments whose sequence information is obtained are also random for each run (FIG. 6). However, repeating the process as described supra allows each and every nucleotide of the unknown sequence to be identified by the nanopore detector. Thus, the whole unknown sequence can be constructed by overlapping the obtained sequence information of random sections of the ss test DNA.

Figure 7:
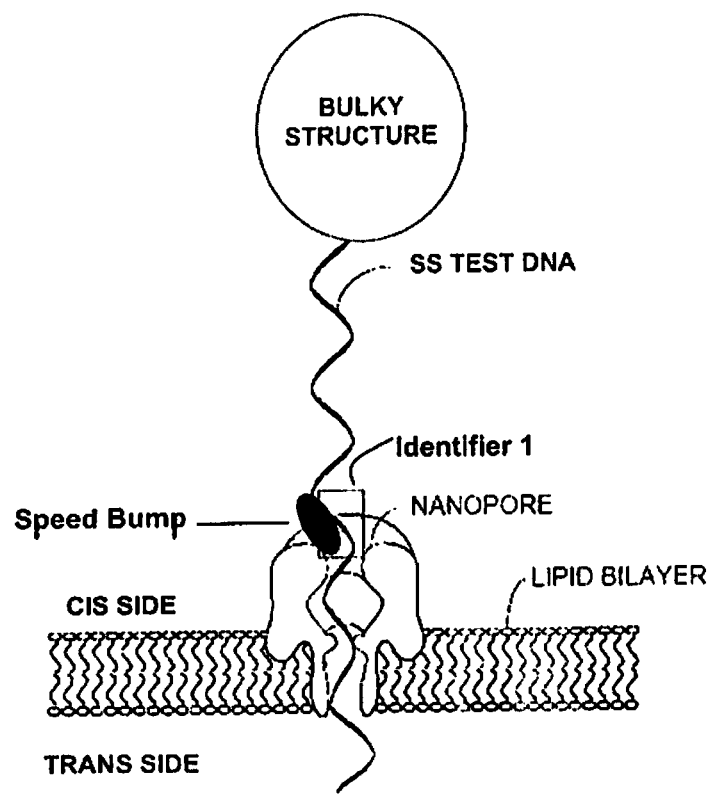
FIG. 7 illustrates a speed bump bound to a ss test DNA having a bulky structure at a first end to stall its passage through a nanopore.

When the ss test DNA comprises one or more known sequences (identifiers), the method described herein can also be used to detect the presence of one or more identifiers and/or to identify a sequence on the ss test DNA that is in front of the identifier in the flow direction of the ss test DNA. The ss test DNA can have BS on only one end (FIG. 7) or both ends as described supra. The nanopore detector can be operated at a working temperature lower than room temperature. A speed bump pool comprises speed bumps that can bind specifically to the identifier (e.g. identifier 1, FIG. 7) to form a speed bump-identifier duplex segment. The speed bump-identifier duplex segment stalls the ss test DNA and a set of electrical signals are obtained. These signals can be characterized to show presence of the identifier or to identify the sequence of the segment before the identifier in the flow direction of the ss test DNA.

Identification of an Unknown Sequence Using a Random Speed Bump Pool

One aspect of the invention relates to a method of identifying an unknown sequence in a test DNA molecule, comprising:

(B1) forming a first bulky structure (BS1) on a first end of the test DNA molecule, (B2) applying an electric potential to flow the test DNA molecule through a nanopore, (B3) forming a second bulky structure (BS2) on a second end of the test DNA molecule, (B4) optionally applying another electric potential to reverse the flow of the test DNA until the test DNA is stopped by BS2 before the constriction area of the nanopore, (B5) contacting a pool of speed bumps (speed bump pool) with the test DNA molecule to form a speed bump-test DNA molecule complex having at least one speed bump-test DNA molecule segment, (B6) applying another electric potential to flow the speed bump-test DNA molecule complex through the nanopore until a first speed bump-test DNA molecule segment is stalled before the constriction area of the nanopore, (B7) obtaining a first set of electrical signals when the first speed bump-test DNA molecule segment is stalled inside the nanopore for a dwelling time, and characterizing the nucleotide sequence that is in front of the first speed bump-test DNA molecule segment and the first basepair of the first speed bump-test DNA molecule segment, in the flow direction of the test DNA molecule, (B8) dissociating the first speed bump-test DNA molecule segment and continuing the flow of the test DNA molecule through the nanopore, and (B9) repeating steps (B4)~(B8) until the test DNA molecule is stopped by BS1 or BS2.

In one embodiment, the test DNA molecule is a ss test DNA comprising one or more nucleotides as defined below. Speed bumps comprise one or more nucleotides as defined below.

As used herein, a nucleotide can be a primary nucleotide or a nucleotide analog. A primary nucleotide is deoxyadenosine mono-phosphate (cAMP), deoxycytidine mono-phosphate (dCMP), deoxyguanosine mono-phosphate (dGMP) or deoxythymidine mono-phosphate (dTMP). A nucleotide analog is an analog or mimic of a primary nucleotide having modification on the primary nucleobase (A, C, G and T), the deoxyribose structure, the phosphate group of the primary nucleotide, or any combination thereof. For example, a nucleotide analog can have a modified base, either naturally existing or man-made. Examples of modified bases include, without limitation, methylated nucleobases, modified purine bases (e.g. hypoxanthine, xanthine, 7-methylguanine, isodG), modified pyrimidine bases (e.g. 5,6-dihydrouracil and 5-methylcytosine, isodC), universal bases (e.g. 3-nitropyrrole and 5-nitroindole), non-binding base mimics (e.g. 4-methylbezimidazole and 2,4-diflurotoluene or benzene), and no base (abasic nucleotide where the nucleotide analog does not have a base). Examples of nucleotide analogs having modified deoxyribose (e.g. dideoxynucleosides such as dideoxyguanosine, dideoxyadenosine, dideoxythymidine, and dideoxycytidine) and/or phosphate structure (together referred to as the backbone structure) includes, without limitation, glycol nucleotides, morpholinos, and locked nucleotides.

The ss test DNA comprises an unknown sequence whose nucleic acid sequence is to be identified by the method described herein. The unknown DNA can be a natural DNA obtained from a biological sample or a synthetic DNA. The synthetic DNA may be a DNA obtained by modification of a natural DNA, such as pre-processed DNA intended for use in DNA identification and/or sequencing. Examples of such pre-processings include, without limitation, enrichment of the unknown DNA for desired fragments, paired-end processing, mated pair read processing, epigenetic pre-processing including bisulfide treatment, focused fragment analysis via PCR, PCR fragment sequencing, and short DNA fragment analysis.

In one embodiment, the unknown sequence has 1 to about 10,000 bases, 1 to about 1,000 bases, 1 to about 500 bases, 1 to about 300 bases, 1 to about 200 bases, 1 to about 100 bases, about 5 to about 10,000 bases, about 5 to about 1,000 bases, about 5 to about 500 bases, about 5 to about 300 bases, 5 to about 200 bases, 5 to about 100 bases, 10 to about 10,000 bases, 10 to about 1,000 bases, 10 to about 500 bases, 10 to about 300 bases, 10 to about 200 bases, 10 to about 100 bases, 20 to about 10,000 bases, 20 to about 1,000 bases, 20 to about 500 bases, 20 to about 300 bases, 20 to about 200 bases, 20 to about 100 bases, 30 to about 10,000 bases, 30 to about 1,000 bases, 30 to about 500 bases, 30 to about 300 bases, 30 to about 200 bases, 30 to about 100 bases, 50 to about 10,000 bases, 50 to about 1,000 bases, 50 to about 500 bases, 50 to about 300 bases, 50 to about 200 bases, or 50 to about 100 bases.

A random speed bump pool comprises a collection of speed bumps of a given length that can bind to all sections of the ss test DNA or a fragment thereof (e.g. an unknown DNA). Such a given length can be 2, 3, 4, 5, 6, 7, 8, 9, 10, 11, 12, 13, 14, 15, or 16, preferred 10 or less, 8 or less, 6 or less and 4 or less. In one embodiment, the random speed bump pool comprise speed bumps composed of one or more nucleotides selected from the group consisting of universal nucleotides, locked nucleotides, primary nucleotides, modifications thereof, and combinations thereof. Modifications of universal nucleotides, and primary nucleotides include modifications at the nucleobase structures, the backbone structures (e.g. glycol nucleotides, morpholinos, and locked nucleotides) and combinations thereof. In a preferred embodiment, the random speed bump pool comprises oligonucleotides having universal nucleobases which base-pair with all primary nucleobases (A, T, C and G). In another preferred embodiment, the random speed bump pool comprises oligonucleotides having all possible combinations of primary nucleobases. In another preferred embodiment, the random speed bump pool comprises oligonucleotides having all possible combinations of primary nucleobases and universal nucleobases. In another preferred embodiment, the random speed bump pool comprises oligonucleotides having universal nucleotides at designated positions and all combinations of primary nucleobases at the other positions. In another preferred embodiment, the backbone structures of the speed bumps in the random speed bump pool are modified (e.g. glycol nucleotides, morpholinos, and locked nucleotides) at designated position(s), random positions or combinations thereof.

The speed bumps comprise universal nucleobases at designated positions and random primary nucleobases at other positions to lower the total number of possible combinations of primary nucleobases. For example, for a random speed bump pool having 10-base oligonucleotides, the total amount of combinations of the primary nucleobases is $4^{10}$=1,048, 576. However, if 4 positions of the 10-base nucleotide are designated to have universal nucleobases only, the total amount of combinations of the primary nucleobases is $4^6$=4, 096, which is significantly lower.

In certain embodiments, because the first base pair of the speed bump-test DNA duplex segment may be partially or completely in the nanopore and influence the electrical signals obtained, it is preferred to construct the speed bumps to have a universal nucleotide at the 5' and/or 3' end to normalize the contribution of the first base pair of the speed bump-test DNA duplex segment and makes the signals easier to analyze.

In certain embodiment, the concentrations of one or more speed bumps of a random speed bump pool may be further adjusted to as desired. For example, the concentrations may be about the same for each type of speed bump; and be adjusted such that sufficient ss speed bumps exist to contact the ss test DNA. In one embodiment, because polyG strands bind strongly to polyC strands, polyG and polyC speed bumps will have higher concentrations than speed bumps having other sequences to provide sufficient ss polyG and ss polyC to contact the ss test DNA. In another embodiment, the concentrations of speed bumps and/or nucleotides used to make the speed bumps are adjusted such that each speed bump has about the same affinity to form speed bump-test DNA complex, and no specific speed bumps are significantly more favored than others. In certain embodiments, the concentrations of speed bumps and/or nucleotides used to make the speed bumps are adjusted such that one or more specific speed bumps are significantly more favored than others. For example, the speed bump pool can be constructed to be substantially free of speed bumps that can bind to known segments in the ss test DNA. Therefore, more sequence information obtained will be about the unknown segments and not the known segments in the ss test DNA.

In certain embodiments, PB1 and/or PB2 comprise(s) structures that are non-binding to speed bumps in the speed bump pool. Examples of such structures include, without limitation, nucleotide analogs comprising non-binding bases such as IsodG, IsodC and abasic site.

In certain embodiments, step (B5) forms a speed bump-test DNA complex having at least one speed bump-test DNA duplex segment, wherein the speed bump forms a duplex with the ss test DNA segment that is up to 1, 2, 3, 4, 5, 6, 7, 8, 9, 10, 11, 12, 13, 14, 15, or 16 basepairs, and is threaded in the nanopore at a first working condition. A working condition includes parameters such as a working temperature (Tw), exposure time, concentration of speed bump and ss test DNA, pH, salt concentration, and other additives and concentration thereof that can affect the formation of speed bump-test DNA complex. Tw is about −10 to about 25° C., about −10 to about 20° C., about −10 to about 15° C., about −10 to about 10° C., about −10 to about 5° C., about −10 to about 0° C., about −10 to about −5° C., about −5 to about 25° C., about −5 to about 20° C., about −5 to about 15° C., about −5 to about 10° C., about −5 to about 5° C., or about −5 to about 0° C., to allow association of relatively short speed bumps (2, 3, 4, 5, 6, 7, 8, 9, 10, 11, 12, 13, 14, 15, or 16 bases) to the ss test DNA. In one embodiment, Tw is about at least 10° C. lower, preferably at least about 20° C. lower than T2. In another embodiment, at Tw, at least about 50% of PB1 and PB2 are in the forms of BS1 and BS2, respectively. In another embodiment, at Tw, at least about 70% of PB1 and PB2 are in the forms of BS1 and BS2, respectively. In another embodiment, at Tw, at least about 90% of PB1 and PB2 are in the forms of BS1 and BS2, respectively.

Exposure time of ss test DNA to speed bumps is about 1 ns or longer, about 10 ns or longer, about 1 µs or longer, about 10 µs or longer, about 1 ms or longer, about 10 ms or longer, about 1 s or longer, or about 5 s or longer to allow sufficient speed bump-test DNA complex to form. Concentrations of the speed bumps are preferably about 100,000 times, 10,000 times, 1,000 times, 300 times, about 200 times, about 100 times, about 50 times, or about 20 times of the concentration of the ss test DNA, or the concentration of the speed bumps is about the same as that of the ss test DNA. The concentrations of the speed bumps are preferably about 1 nM~about 100 mM, about 1 nM~about 10 mM, about 1 nM~about 1 mM, about 10 nM~about 100 mM, about 10 nM~about 10 mM, about 10 nM~about 1 mM, about 1 mM~about 10 mM, or about 10 mM~100 mM. The concentration of ss test DNA is about 1 nM~about 100 mM, about 1 nM~about 10 mM, about 1 nM~about 1 mM, about 10 nM~about 100 mM, about 10 nM~about 10 mM, or about 10 nM~about 1 mM. pH is preferably about 6~about 8, or about 7. Salt (e.g. KCl, NaCl, phosphate) concentration is about 1 mM to about 10 M, about 1 mM to about 1 M, about 10 mM to about 10 M, about 10 mM to about 1 M, about 100 mM to about 10 M, or about 100 mM to about 1 M. Other additives that may affect the formation of speed bump-test DNA complex include, without limitation, dextran sulfate and glycerol. Their concentrations may be adjusted to optimize formation of speed bump-test DNA complex.

A working condition further comprises an electric potential of about −320 mV to about 320 mV at a desired polarity. The working condition can be continuously adjusted through the process based on the characteristics of the speed bump binding (e.g. length, nucleotide components, and binding affinity), the nanopore characteristics and the ss test DNA property (e.g. GC content or secondary structure thereof), to optimize the signal quality. Thus, the electric potential can continuously change from for example, −320 mV to +320 mV.

Steps (B4)~(B9) are carried out at a first working condition as described supra. In certain embodiments, the electric potential applied to each step of steps (B4)~(B9) may be the same or different or continuously changing. In certain embodiment, the electric potential for step (B8) may be adjusted to facilitate the dissociation of the speed bump-test DNA duplex segment. In certain embodiment, the electric potential for step (B8) may be applied to move the ss test DNA at a reduced value or at a reversed polarity compared to the ss test DNA flow direction in step (B6) (forward direction) to move the speed bump-test DNA duplex segment from the constriction area of the nanopore before applying another electric potential to move the DNA at the forward direction to dissociate the speed bump-test DNA duplex segment.

A dwelling time required for a nanopore detector to collect relevant sequence information relates to the nanopore detector and the working condition. In certain embodiments, the dwelling time is at least about 10 μs, at least about 1 ms, at least about 10 ms, at least about 200 ms, at least about 500 ms, at least about 1 s, at least about 2 s, or at about least 5 s. Generally, the longer the dwelling time is, the better the signal quality, and the more sequence information that can be obtained. In certain embodiments, the sequence of up to 5 bases is identified when a speed bump-test DNA duplex segment is stalled in a nanopore. In certain embodiments, the sequence of up to 3 bases is identified when a speed bump-test DNA duplex segment is stalled in a nanopore. In certain embodiments, the sequence of up to 2 bases is identified when a speed bump-test DNA duplex segment is stalled in a nanopore. In certain embodiments, the sequence of 1 bases is identified when a speed bump-test DNA duplex segment is stalled in a nanopore.

As shown in FIG. 4, a ss test DNA comprising bulky structures formed on both ends is locked in a nanopore (steps (B1)~(B4)) and forms speed bump-test DNA complex with multiple speed bumps (step (B5)).

Figure 8:
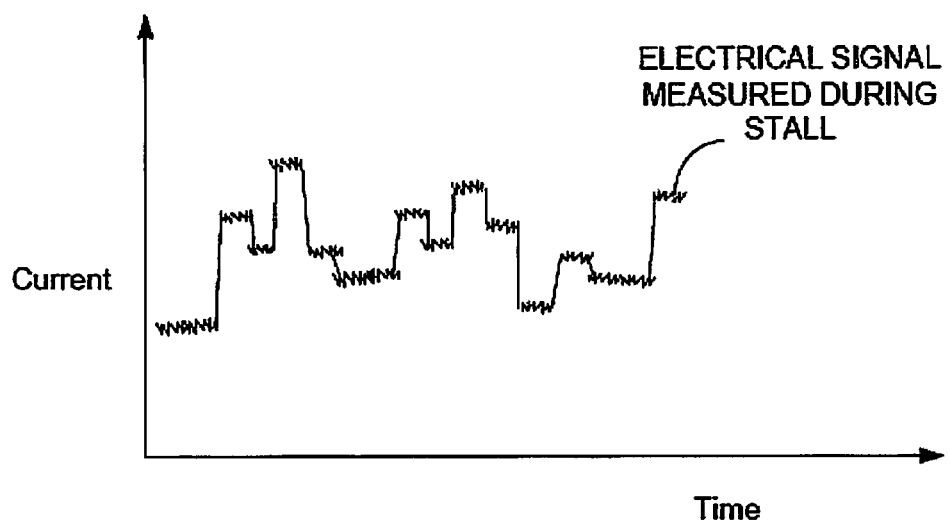
FIG. 8 illustrates multiple sets of electrical signals obtained by a nanopore detector according to the present invention.

A set of electrical signals of the ss test DNA are obtained each time the ss test DNA is stalled by a speed bump-test DNA duplex segment in the nanopore for a dwelling time, and then the speed bump-test DNA duplex segment dissociates and the ss test DNA moves forward until stalled by the next speed bump-test DNA duplex segment. This stall-detect-dis-associate-stall process is repeated until the ss test DNA is stopped by the bulky structure of one end. An example of electrical signals obtained is shown in FIG. 8.

In certain embodiments, a random speed bump pool is present mainly on one side of the nanopore (e.g., Cis side as shown in FIG. 4), and the method further comprising:

(B10) applying another electric potential to move the test DNA at a reversed direction of the test DNA flow in step (B5) until the ss test DNA is stopped by the other bulky structure before the constriction area of the nanopore, (B11) repeating steps (B4)~(B10) at least 1 time, at least 5 times, at least 10 times, at least 15 time, at least 20 time, at least 25 times, at least 30 times, at least 50 times, or at least 100 times and (B12) constructing the test DNA sequence by overlapping the collected nucleotide sequence information.

Step (B10) are carried out under a working condition described supra. The electric potential applied can be at a reduced value or a reverse polarity compared to the electric potential applied in step (B4)~(B9) to reverse the flow of the test DNA. The electric potential applied in each step can be the same or different or continuously changing.

Figure 9:
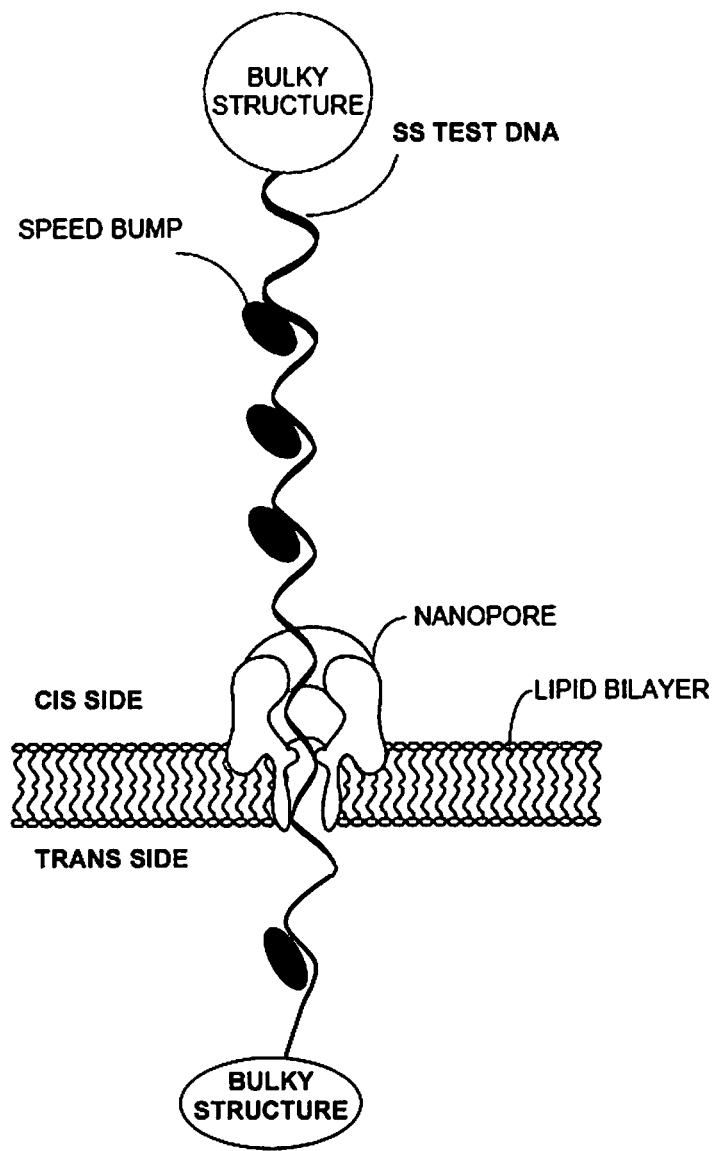
FIG. 9 illustrates a ss test DNA trapped in a nanopore bound with multiple speed bumps on both sides of the nanopore.

In certain embodiments, a random speed bump pool is present in both sides of the nanopore and speed bumps bind to the ss test DNA at the segment exposed to the speed bump pool in both sides of the nanopore (Cis and Trans sides as shown in FIG. 9). The method of identifying a nucleotide sequence of an unknown DNA in a ss test DNA described herein further comprising:

(1) repeating steps (B4)~(B8) under a second working condition until the ss test DNA is stopped by the other bulky structure before the constriction area of the nanopore.

(2) repeating steps (B9) and (1) at least 1 time, at least 5 times, at least 10 times, at least 15 time, at least 20 time, at least 25 times, at least 30 times, at least 50 times, at least 100 times; and (3) constructing the nucleic acid sequence of the unknown DNA by overlapping the collected nucleotide sequence information.

The second working condition is a working condition as described supra. The second working condition can have the same or different parameters compared to the first working condition. The electric potential applied in step (1) can be at a reduced value or a reversed polarity compared to the electric potential applied in step (B9). The electric potential applied in each step can be the same as applied in the earlier step, or different compared to the earlier step, or continuously changing.

Because a random speed bump pool comprises speed bumps that can bind to random sections of the ss test DNA, each time when the ss test DNA goes from one end stopped by BS1/BS2 to the other end according to the process described herein, speed bumps may bind to different combinations of ss test DNA duplex segments (FIG. 5), and can provide sequence information of different segments in the ss test DNA (FIG. 6). Thus, when step (B8) and/or step (B9) are/is repeated such that sequence information of each and every nucleotide of the unknown DNA in the ss test DNA has been obtained, the unknown DNA can be constructed by overlapping the collected nucleotide sequence information.

In certain embodiments, a ss test DNA comprises known identifier segments as described supra. The ss test DNA can be constructed such that the identifier segments will not be bound by the random speed bump pool. For example, an identifier segment can have isodG and isodC bases which preferably bind to each other. If speed bumps of the random speed bump pool do not have isodG or isodC base, speed bumps from the random speed bump pool will more preferably bind to section of the test DNA that is outside of the identifier segments. Thus, fewer electrical signals will be collected relating to the sequence information of the identifier, which makes the collected electrical signals easier to characterize.

Figure 10:
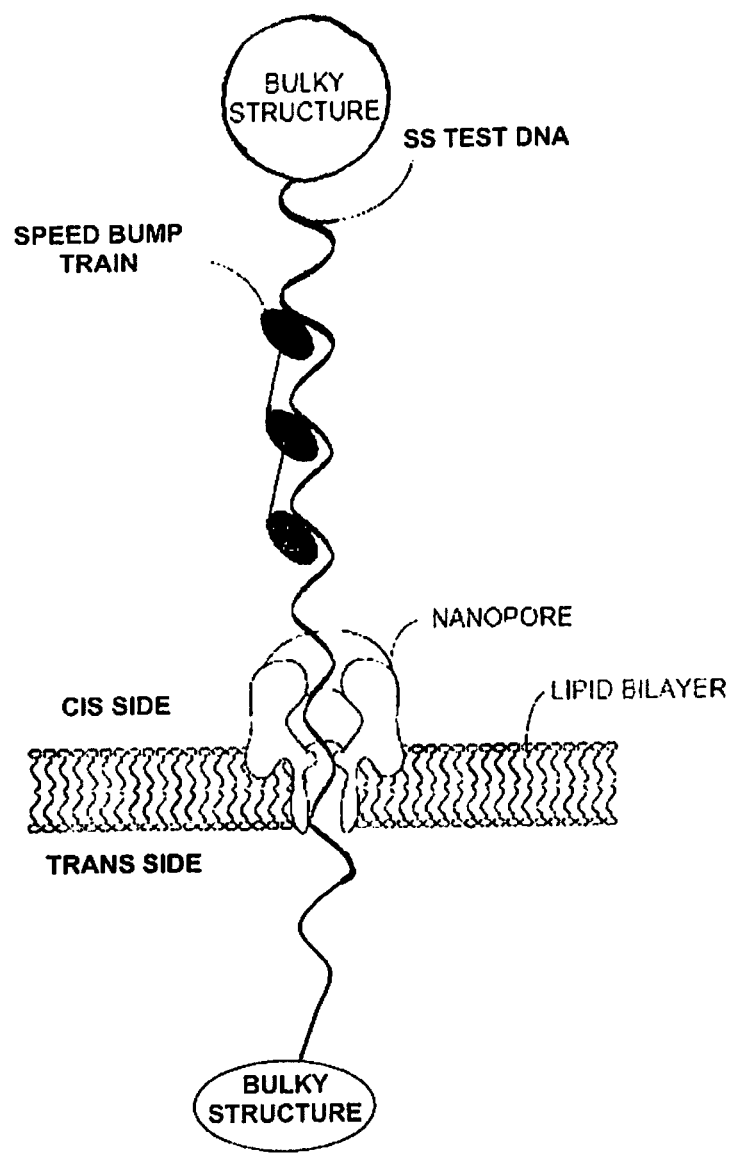
FIG. 10 illustrates contacting a ss test DNA with a speed bump train.

In certain embodiments, more than one speed bump is linked by a non-biding linker (e.g. abasic oligonucleotide) to form speed bump train (FIG. 10) such that the dissociation of each speed bump-test DNA duplex segment will not cause the dissociation of the whole speed bump train from the ss test DNA. In certain embodiments, the non-binding linker is designed to be spaced by about 1 base, about 2 bases, about 3 bases, about 4 bases or about 5 bases. Thus, the gap between known segments shown in FIG. 6 will be more likely to be the same as the length of the linker (e.g. about 1 base, about 2 bases, about 3 bases, about 4 bases or about 5 bases). It will be easier to construct the nucleic acid sequence of the unknown DNA in this case.

Figure 11:
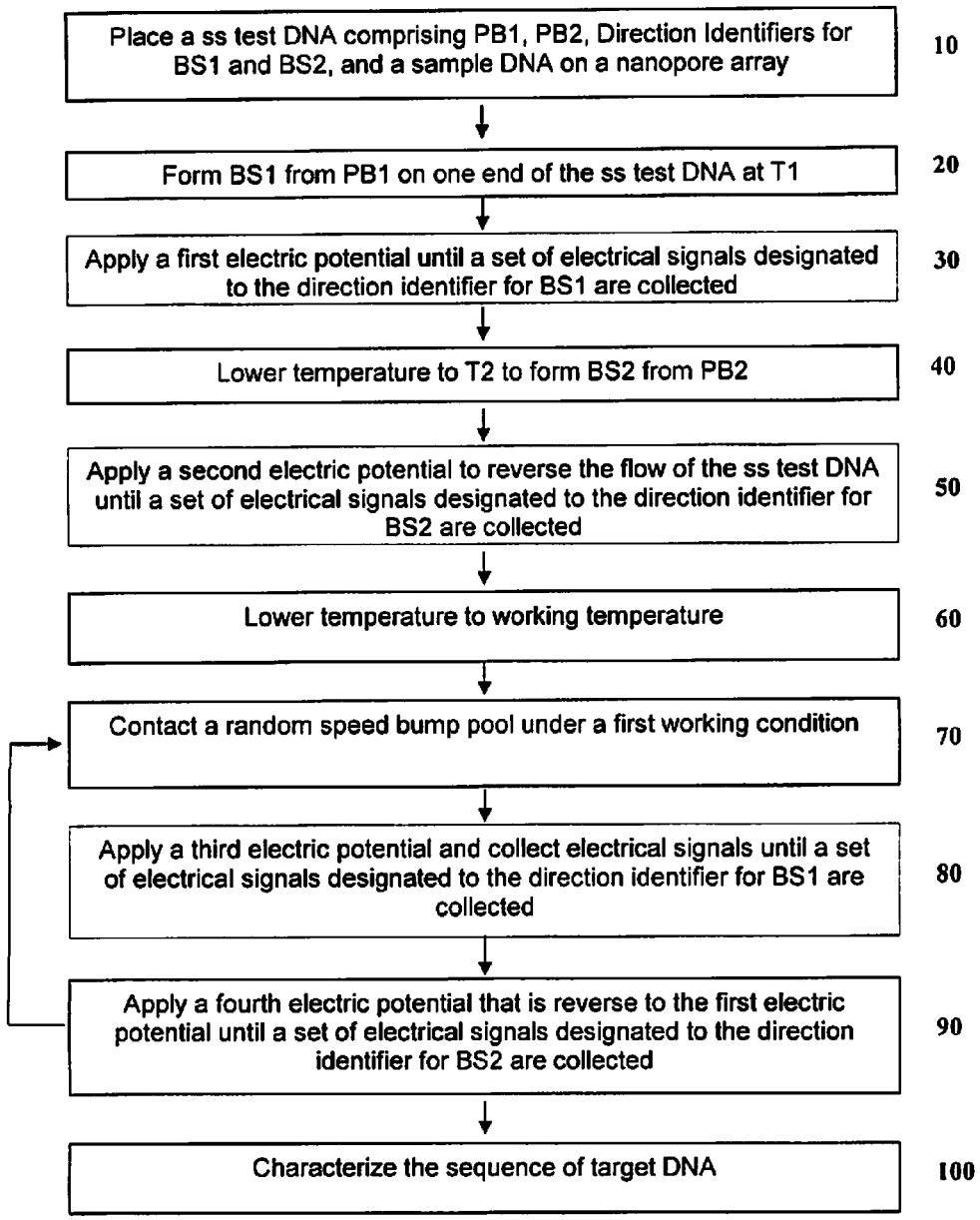
FIG. 11 illustrates a flowchart of a process according to one embodiment of the present disclosure.

In one embodiment, a method as described herein is carried out according to a flowchart shown in FIG. 11. A ss test DNA comprising PB1, PB2, DI1, DI2 and an unknown DNA has been constructed and placed on nanopore array (Block 10, FIG. 11). Then BS1 is formed from PB1 on one end of the ss test DNA at T1 (Block 20, FIG. 11). A first electric potential is applied to thread the ss test DNA through a nanopore until the ss test DNA is stopped by BS1 wherein a set of electrical signals characterizing DI1 are collected (Block 30, FIG. 11). The temperature is then lowered to T2 to form BS2 from PB2 (Block 40, FIG. 11). A second electric potential that is lower than the first electric potential or opposite in polarity to the first electric potential is applied until the ss test DNA is stopped by BS2 wherein a set of electrical signals characterizing DI2 are collected (Block 50, FIG. 11). The temperature is further lowered to Tw (Block 60, FIG. 11), then contact a random speed bump pool with the ss test DNA under a first working condition as described supra to form randomly bound speed bump-test DNA complex (Block 70, FIG. 11). A third electric potential is applied, moving the speed bump-test DNA complex through the nanopore until the ss test DNA is stalled by a first speed bump-test DNA duplex segment. The ss test DNA is stalled for a dwelling time during which a set of electrical signals are obtained, which will be used to characterize the sequence in front of the first speed bump-test DNA duplex segment and the first base pair of the speed bump-test DNA duplex segment in the flow direction of the ss test DNA. Then the first speed bump-test DNA duplex segment is dissociated and the ss test DNA continues through the nanopore until stopped by the next speed bump-test DNA duplex segment or BS1. A set of electrical signals designated to DI1 are collected when the ss test DNA is stopped by BS1 in the nanopore (Block 80, FIG. 11). Then a fourth electric potential that is at a reduced value or a reverse polarity to the third electric potential is applied until the ss test DNA is stopped by BS2 wherein a set of electrical signals characterizing DI2 are collected (Block 90, FIG. 11). Then the steps in Blocks 70~90 are repeated until sufficient sequence information has been collected to characterize the sequence of the unknown DNA.

Detection of a Segment of Known Structure and Identification of an Unknown Segment Adjacent to a Known Structure in a Test DNA Molecule Another aspect of the invention relates to a method of obtaining sequence information of a ss test DNA molecule as described supra. The method comprises:
(B1) forming a first bulky structure on a first end of the test DNA molecule,
(C1) contacting a pool of speed bumps (speed bump pool) with the test DNA molecule to form a speed bump-test DNA molecule complex having at least one speed bump-test DNA molecule segment,
(C2) applying an electric potential to flow the speed bump-test DNA molecule complex through a nanopore until a first speed bump-test DNA molecule segment is stalled before the constriction area of the nanopore,
(C3) obtaining a first set of electrical signals when the first speed bump-test DNA molecule segment is stalled inside the nanopore for a dwelling time, in the flow direction of the test DNA molecule,
(C4) dissociating the first speed bump-test DNA molecule segment and continuing the flow of the molecule through the nanopore, and
(C5) repeating steps (C1)~(C4) until the test DNA molecule is stopped by BS1.

In one embodiment, the test DNA molecule is a ss test DNA comprising one or more nucleotides as described supra, and the speed bumps comprise one or more nucleotides as described supra. The ss test DNA comprises PB1 as described supra.

In certain embodiments, step (C1) forms a speed bump-test DNA complex having at least one speed bump-test DNA duplex segment, wherein the speed bump forms a duplex with the test DNA duplex segment that is up to 1, 2, 3, 4, 5, 6, 7, 8, 9, 10, 11, 12, 13, 14, 15, or 16 basepairs.

Steps (C1)~(C5) are carried out at a working condition as described supra.

A dwelling time required for a nanopore detector to collect relevant sequence information is the same as described supra.

In certain embodiments, the method further comprising:
(C6) according to the first set of electrical signals obtained in step (C3) and/or the electrical signals obtained from step (C5),
indicating the ss test DNA comprises the identifier segment, and/or
characterizing the nucleotide sequence that is in front of the speed bump-identifier duplex segment and the nucleotide sequence of the first basepair of the speed bump-test DNA duplex segment, in the flow direction of the ss test DNA.

In certain embodiments, the method described herein is used to detect an identifier exists in the ss test DNA. An identifier can serve as e.g. direction identifier (e.g. verifying the formation of BS1 and showing the ss test DNA has reached to the end having BS1), reference signal identifier (a reference or calibration read to base line other electrical signals obtained in the same nanopore), sample source identifier (identifying the source of the test DNA), or sample identifier for the test DNA (identifying the test DNA). In certain embodiments, a speed bump pool comprises a first speed bump (FIG. 7) which can bind to a first identifier (identifier 1 in FIG. 7), and is substantially free of other speed bumps that can bind to the ss test DNA (preferably less than 10%, more preferably less than 5%, and most preferably less than 1%).

When a ss test DNA comprising identifier 1 contacts the first speed bump, a first speed bump-identifier 1 duplex segment is formed to form a first speed bump-test DNA complex. In the presence of an appropriate electrical field, the first speed bump-test DNA complex goes through a nanopore until stalled by the first speed bump-identifier 1 duplex segment. The nanopore detector obtains a first set of electrical signals. Then the first speed bump-test DNA complex dissociates and the ss test DNA goes through the nanopore until stopped by BS1 at the first end (i.e. in step (C4), the ss test DNA flow through the nanopore smoothly until stopped by BS1 without being stalled again in the nanopore). The nanopore detector will obtain another set of electrical signals when the ss test DNA is stopped by the BS1 structure. Thus, compared to a ss test DNA that does not comprise identifier 1 sequence, the ss test DNA that comprises identifier 1 sequence provides two sets of electrical signals showing that it is stalled twice in the nanopore, while the ss test DNA that does not comprise identifier 1 sequence provides one set of electrical signals showing it is stalled once in the nanopore (by BS1).

In another embodiment, the ss test DNA and/or the speed bumps can be constructed such that the first set of electrical signal obtained in step (C3) is distinctive from a set of electrical signals obtained when a primary nucleotide sequence is detected by the nanopore. For example, the known identifier sequence can comprise one or more nucleotide analogs having isodG and/or IsodC. In front of this identifier sequence is a known reading sequence that would be in the constriction zone of a pore if a speed bump was hybridized to the identifier sequence and stopped in the pore. The reading sequence may comprise IsodC, IsodG and/or abasic nucleotides that do not bind to natural nucleotides. Additionally, both the identifier sequence and the specific antisense speed bump sequence to the identifier would contain appropriate IsodG and IsodC so that only the specific speed bump to the identifier would hybridize to that location. Natural nucleotide speed bumps would not interfere or bind to the IsodG, IsodC-containing identifier sequence and natural nucleotide speed bumps would not interfere with the reading sequence. The resulting identification of the strand in the pore would occur independent of the presence of other natural or man-made nucleotide speed bumps. In this case, the speed bump pool does not have to be substantially free of other speed bumps that can form complex with the ss test DNA. When another speed bump binds to a segment of the ss test DNA other than identifier 1 segment, the first set of electrical signal obtained while the first speed bump-test DNA duplex segment is stalled in the nanopore is distinctive from the other set of electrical signal obtained while the other speed bump-test DNA duplex segments are stalled in the nanopore. Thus, the presence of other speed bumps that can form complex with the ss test DNA does not interfere with the detection of the distinctive signals generated from binding of the first speed bump with identifier 1 of the ss test DNA. The ss test DNA and/or the speed bumps can be further constructed such that no other speed bumps binds to the identifier 1 segment as described supra. Thus, other speed bumps that do not comprise isodG or isodC bases will not bind to the identifier 1 segment.

In another embodiment, the ss test DNA comprises more than one identifier, and the ss test DNA and/or the speed bumps (SBN, N=1, 2, . . . ) that bind to the identifier segments (identifier N) respectively are designed such that when each SBN-identifier N duplex segment is stalled in the nanopore, the set of electrical signal obtained from the nanopore is distinctive from a primary nucleotide sequence and from when other SBN-identifier N duplex segment is stalled in the nanopore. The speed bump pool comprises the speed bumps-specific for the identifier(s) that is(are) to be detected, and optionally include speed bumps for other identifiers and/or other speed bumps that can bind to the ss test DNA.

In another embodiment, the identifier that binds to the identifier-specific speed bump and the sequence in front of the identifier in the flow direction of the ss test DNA are both known. Thus, the set of electrical signals obtained in step C3 can also be used to identify the sequence in front of the identifier in the flow direction of the ss test DNA, which can in turn be used to identify of the identifier.

In another embodiment, an identifier is placed adjacent to an unknown segment in the ss test DNA. In one embodiment, the identifier is adjacent to the 5' end of the unknown segment in the ss test DNA. BS1 is on the 5' end such that the ss test DNA can only enter the nanopore from its 3' end. The speed bump-identifier duplex segment is formed and stalled in the nanopore under the application of an electric potential, and a set of electrical signal can be obtained to provide sequence information of the nucleotide sequence that is in front of the speed bump-identifier duplex segment and the first basepair of the speed bump-identifier duplex segment. In another embodiment, the identifier is adjacent to the 3' end of the unknown segment in the ss test DNA. BS1 is on the 3' end such that the ss test DNA can only enter the nanopore from its 5' end. The speed bump-identifier duplex segment is formed and stalled in the nanopore under the application of an electric potential, and a set of electrical signal can be obtained to provide sequence information of the nucleotide sequence that is in front of the speed bump-identifier duplex segment and the first basepair of the speed bump-identifier duplex segment. In certain embodiments, the unknown sequence has up 1 base, 2 bases, 3 bases, 4 bases, or 5 bases.

In another embodiment, the method further comprises applying a first electric potential to flow the ss test DNA through a nanopore, and forming a second bulky structure (BS2) on a second end of the ss test DNA under a second condition as described supra. In one embodiment, the temperature of the first condition (T1) is higher than the temperature of the second condition (T2), which is higher than the working temperature Tw. In a preferred embodiment, the temperature of the first condition (T1) is at least 10° C. higher or at least 20° C. higher than the temperature of the second condition (T2), which is at least about 1° C. higher, at least about 5° C. higher, at least about 10° C. higher, at least about 15° C. higher, at least about 20° C. higher, or at least about 25° C. higher than the working temperature Tw.

In certain embodiments, the identifier sequence that is adjacent to the unknown DNA is contacted with a first known speed bump (e.g. 2, 3, 4, 5, 6, 7, 8, 9, or 10 bases long), and the unknown DNA sequence that is in front of the identifier-speed bump duplex in the first flow direction of the ss test DNA molecule can be identified. Extending the sequence of the known speed bump in the flow direction of the ss test DNA allows identification of longer sequences in the unknown DNA. This method comprises the following steps:

(E1) contacting a first known speed bump with the test DNA molecule to form a first known speed bump-test DNA molecule complex having a first known speed bump-test DNA molecule segment, (E2) applying an electric potential to flow the first known speed bump-test DNA molecule complex through a nanopore until the first known speed bump-test DNA molecule segment is stalled before the constriction area of the nanopore, (E3) obtaining a first set of electrical signals when the first known speed bump-test DNA molecule segment is stalled inside the nanopore for a dwelling time, in the flow direction of the test DNA molecule, (E4) dissociating the first known speed bump-test DNA molecule segment and continuing the flow of the molecule through the nanopore, (E5) removing the first known speed bumps from the nanopore detector system and reversing the flow of the test DNA until stopped by the bulky structure at the end, and (E6) repeating steps (E1)~(E5) with another known speed bump having a sequence of the first known speed bump plus a known number of bases longer in the flow direction of the test DNA molecule of step (E3), wherein:

E-a) the known number is 1, 2, 3, 4, 5, 6, 7, 8, 9, or 10,

E-b) the known number of bases can be universal bases or bases that are complementary to the bases at the corresponding positions of the unknown DNA, and E-c) the condition of step (E4) may be adjusted, e.g. raising the working temperature and/or increasing the electric potential value applied in step (E4) to dissociate the speed bump-test DNA molecule segment successfully Although the method described supra can only identify a sequence of the unknown DNA not longer than 15 bases. Such knowledge may facilitate identification/sequencing of the rest of the unknown sequence of the unknown DNA using the method described supra (e.g. using a random speed bump pool). Furthermore, the same process can be used to identify a sequence of the unknown DNA from another end. Thus, up to 30 bases of an unknown DNA can be identified, which will provide a good reference in further identification/sequencing of the whole sequence of the unknown DNA.

Design and Construction of a Test DNA Molecule

A test DNA comprising an unknown sequence can be designed as described supra to comprise one or more functional moieties such as PB1, PB2, and identifiers as described supra.

PB1, PB2 and identifiers have been described supra.

The unknown sequence may be a synthesized DNA or DNA obtained from a biological sample as described supra. The test DNA molecule is constructed by ligating the unknown DNA with other segments as desired using conventional organic and/or biological methods.

The test DNA can be formed by linking multiple functional moieties to an unknown DNA using conventional ligation methods (e.g. formation of covalent bonds (e.g. ligase assisted ligation or other covalent bonds, wherein the ligation can be accomplished by paired end sequencing chemistry, blunt-ended DNA ligation, and/or sticky-end ligation) or non-covalent interactions).

In certain embodiments, the unknown DNA obtained is a double-stranded (ds) unknown DNA. The ds unknown DNA can be ligated with one or more ds functional moieties (e.g. ds PB1, ds PB2, ds identifiers etc.) all in one step, or sequentially, or all functional moieties on one end of the unknown DNA are constructed together first and then ligated to the end of the unknown DNA. Examples of the conventional ligation methods includes, without limitation, ligase assisted ligation following blunt end, dangling end, and/or linker ligation; paired end sequencing protocols; mate-paired and end-paired protocols. Then the obtained ds test DNA is denatured to provide ss test DNA using conventional methods.

In certain embodiments, the unknown DNA obtained is a ds unknown DNA, and is linked to one or more ds functional moieties (e.g. ds PB1, ds PB2, ds identifiers etc.) via covalent bonds other than the phosphodiester bonds. Examples of such linkage include, without limitation, the linkage in glycol nucleotides, morpholinos, and locked nucleotides.

In certain embodiments, the unknown DNA obtained is a ss unknown DNA, and its complementary strand can be created to anneal with the ss unknown DNA to form a ds unknown DNA using conventional methods, and then ligate to one or more ds functional moieties as described supra.

In certain embodiment, a ss unknown DNA is linked to one or more ss functional moieties (e.g. ss PB1, ss PB2, ss identifiers etc.) using ligase assisted ligation. In certain embodiments, a ss unknown DNA is linked to one or more ss functional moieties via covalent bonds other than the phosphodiester bonds. Examples of such linkage include, without limitation, the linkage in glycol nucleotides, morpholinos, and locked nucleotides.

In certain embodiment, the unknown DNA obtained is a ds unknown DNA and can be denatured to provide a ss unknown DNA to be linked to one or more ss functional moieties as described supra.

In certain embodiments, the functional moieties are linked by cleavable bonds such that one or more individual functional moieties can be cleaved from the ss test DNA. In one embodiment, a bulky structure can be removed from a ss test DNA by cleaving a functional moieties positioned between the unknown DNA and the bulky structure. Then, the ss test DNA can be released from the nanopore it is in by applying an electric potential to move the ss test DNA through the nanopore in the direction at which it is no longer stopped by the cleaved bulky structure.

The invention is illustrated further by the following examples that are not be construed as limiting the invention in scope to the specific procedures or products described therein.

EXAMPLES

Example 1

PB2 Structure (I)

Figure 12:
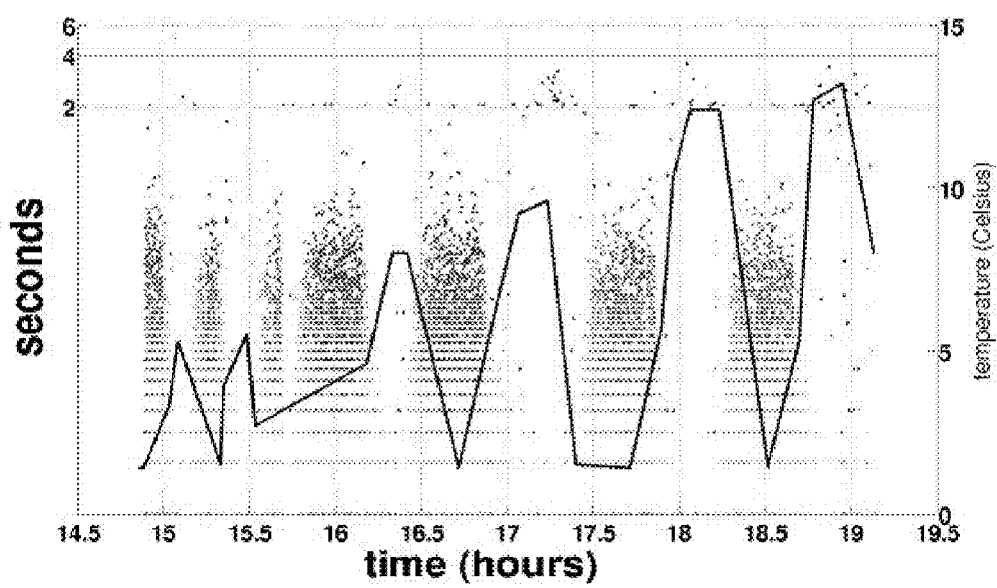
FIG. 12 illustrates the relationship between working temperature and capture of a ss test DNA having BS2-1 on one end and a BS1 on the other end in a nanopore.

A ss test DNA having a BS2 on one end was captured in a nanopore at a temperature lower than T2 and released at a temperature higher than T2 (FIG. 12).

The BS2 (BS2-1) was a DNA 5-base duplex hairpin structure formed from a PB2 having a sequence of 5'-CCCCC CCCCC TTATA CCCCT ATAA-3' (SEQ ID NO. 1, PB2-1). BS2-1 had melting temperature of about 15° C., and a $\Delta G$ of about −0.96 kcal/mol at 5° C. according to the simulation using UNAFOLD program. This moderately low $\Delta G$ indicated that BS2-1 had a relatively low binding energy.

In FIG. 12, the solid line showed the change in temperature from 2° C. to 14° C. The dots represented individual DNA captures, meaning that PB2-1 formed BS2-1 at the corresponding temperature and was captured in the nanopore. The captures were present when the temperature was about or lower than T2 (about 5° C.), indicating that BS2-1 was formed from PB2-1 and the DNA was stalled in the nanopore. The capture of the DNA disappeared when the temperature increased to about 5~10° C. over T2, indicating that BS2-1 melted and was no longer stalled in the nanopore.

Thus, PB2-1 formed BS2-1 which stopped the ss DNA in the pore at temperatures about 10° C. lower than its melting temperature. This may be due to the relatively low $\Delta G$ BS2-1 had. Thus, the DNA duplex structure in BS2-1 was relatively easy to dissociate in the nanopore. Thus, a BS2 having a higher $\Delta G$ may be more difficult to destruct and may provide longer dwelling time at the nanopore at a temperature closer to the melting temperature of the BS2.

Example 2

PB1 and PB2 Structure (II)

A PB1 forms a BS1 at a first temperature (T1) that is higher than the second temperature (T2) at which a BS2 is formed from a PB2. T2 is higher than a working temperature (Tw). In this example, Tw is below room temperature. Thus, PB1 is designed to have a relative long DNA duplex segment (either in a DNA duplex with an anti-sense DNA segment, or in a hairpin structure) such that the desired melting temperature of the relative long DNA duplex segment is achieved.

PB2 is designed to have a lower melting temperature and a high binding energy (ΔG=about −1∼−5 kcal/mol, about −4∼−6 kcal/mol, about −4∼−5 kcal/mol, about −4.5 kcal/mol, or about −4.0 kcal/mol at the working condition). A molly bolt or branched molecule has been designed to provide a BS2 having low T2 while not easily dissociated at the working condition.

An example of PB1 has a sequence of 15 bases and a 4 base A loop; 5'-CGTCT AGCGT TGCCG AAAAC GGCAA CGCTA GACG-3' (SEQ ID NO. 2, PB1-1). This sequence has a delta G of −22.7 kcal/mole and a melt temperature of 91.4° C. in 1 M KCl, and 1 µM sequence concentration according to the simulation using UNAFOLD program.

An example of PB2 has a sequence of 5'-GACCC TGCCC CCAGC TTTCC CCAAA CGTCA AAAAA-3' (SEQ ID NO. 3, PB2-2) and the formed BS2-2 is a 3 stem, 3 duplex, 2 loop molecule as shown below according to the simulation using UNAFOLD program:

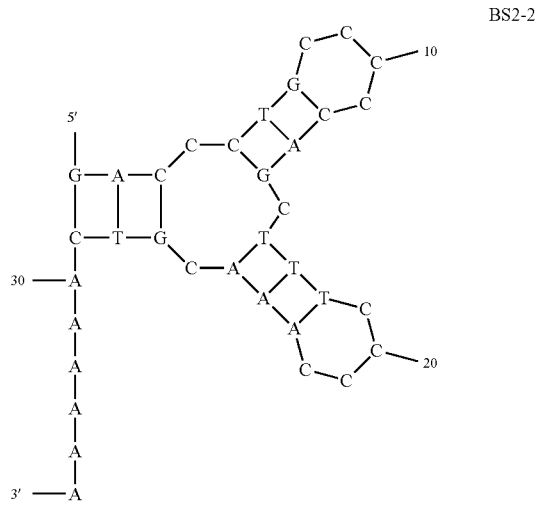

BS2-2

The following characteristics of the BS2-2 were provided using UNAFOLD program:
ΔG=−4.5140 kcal/mol at 5° C. (100% folded),
ΔH=−67.90 kcal/mol,
ΔS=−227.9 cal/(K·mol) and
Tm=24.8083° C.

Figure 13:
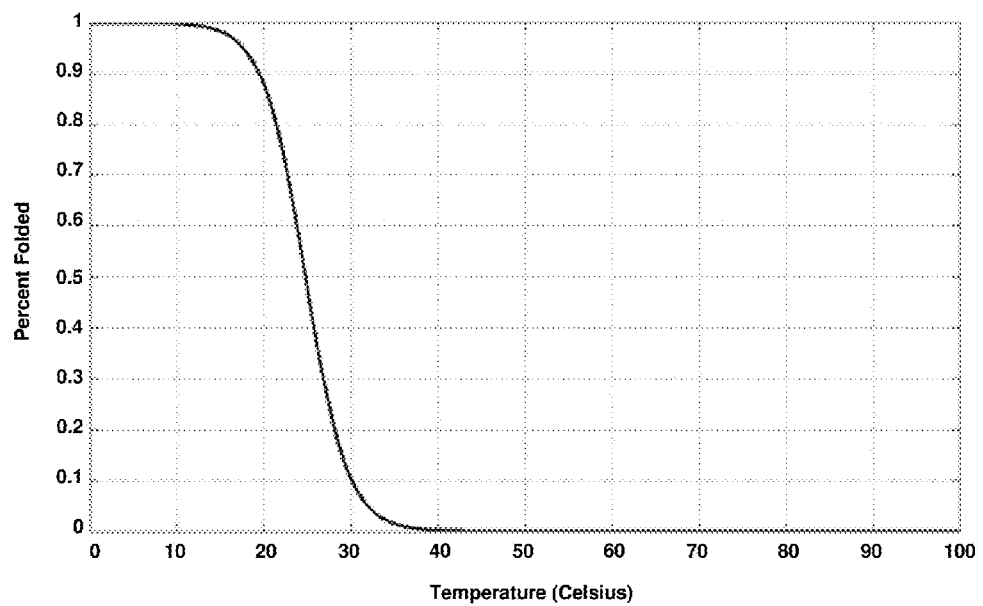
FIG. 13 illustrates a melting curve of an exemplary bulky structure (BS2-2).

A calculated melting curve of BS2-1 was obtained using UNAFOLD and shown in FIG. 13. This melting curve illustrates that at above 30° C. about 90% of the structures are linear (PB2-2) and at below 20° C. about 90% of the structures form BS2-2. Such a steep melting curve shows well controlled bulky structure formation of BS2-2, which is highly desired. The ΔG of BS2-2 at 5° C. is −4.5 kcal/mol, which indicates a stronger binding affinity than the 5 base hairpin molecule BS2-1 in Example 1.

Example 3

Stalling DNA by 4-Base Duplex Segments

This example illustrates a 4-baser duplex segment stalled the ss test DNA in a nanopore for a dwelling time sufficient to obtain desired sequence information.

The test DNAs were the following:

A test DNA was formed by self-hybridization of DNA-1: 5'-CCCCC CCCCC GCGC-3' (SEQ ID NO. 4). DNA-1 was dissolved in biology grade water, heated to 90° C. and then left to cool to room temperature for self-hybridization. A DNA-1 molecule hybridized with another DNA-1 molecule to form a self-hybridized DNA-1 structure having a 4-base GCGC duplex segment at the 3' ends and two overhanging ss 10-C tails at the 5' ends thereof. At the working condition, the self-hybridized DNA-1 structure entered a nanopore with one of the two overhanging ss 10-C tails, stalled in the nanopore by the 4-base duplex segment at the 3' end for a dwelling time, and then when the 4-base duplex segment dissociated, the self-hybridized DNA-1 structure was converted to two ss DNA-1 molecules which went through the nanopore like ss test DNAs. Thus, when flowing through a nanopore, the self-hybridized DNA-1 structure simulated a ss test DNA having a 4-base duplex segment formed by a speed bump and the ss test DNA.

Another test DNA, self-hybridized DNA-2 structure, was formed by self-hybridization of DNA-2: 5'-TTTTT TTTTT GCGC-3' (SEQ ID NO. 5) using the same process described supra regarding the formation of the self-hybridized DNA-1. The self-hybridized DNA-2 structure had a 4-base GCGC duplex at the 3' ends and two overhanging ss 10-T tails at the 5' ends.

Another test DNA was streptavidin-DNA-3 complex formed by incubation of DNA-3: 5'-TTTTT TTTTT TTTTT TTTTT TTTTT TTTTT TTTTT TTTTT-biotin-3' (SEQ ID NO. 6) and streptavidin at a condition described below. When flowing through a nanopore under a electric potential, streptavidin-DNA-3 complex stalled in the nanopore until the electric potential was changed/reversed. Thus, streptavidin-DNA-3 complex served as a positive control showing that the nanopore detector system was working properly. The dwell time of this molecule was long, represented by the points at the far right side of the x-axis (time) in FIG. 14.

The working condition was 20 mM HEPEs buffer and 1 M KCl at 0° C. The electric potential applied was about 128 mV.

The nanopores were created from 10 ng/mL alpha hemolysin deposited onto the surface of a bilayer at a final concentration of 0.2 ng/mL and with the application of electrical stimulus as described in US Application Publication No. 2011/0193570. The bilayers were created with the painting method from 10 mg/mL of DPhPC in Decane across the essentially planar AgCl electrode on a Teflon surface as described in US Application Publication No. 2011/0193570.

Figure 14:
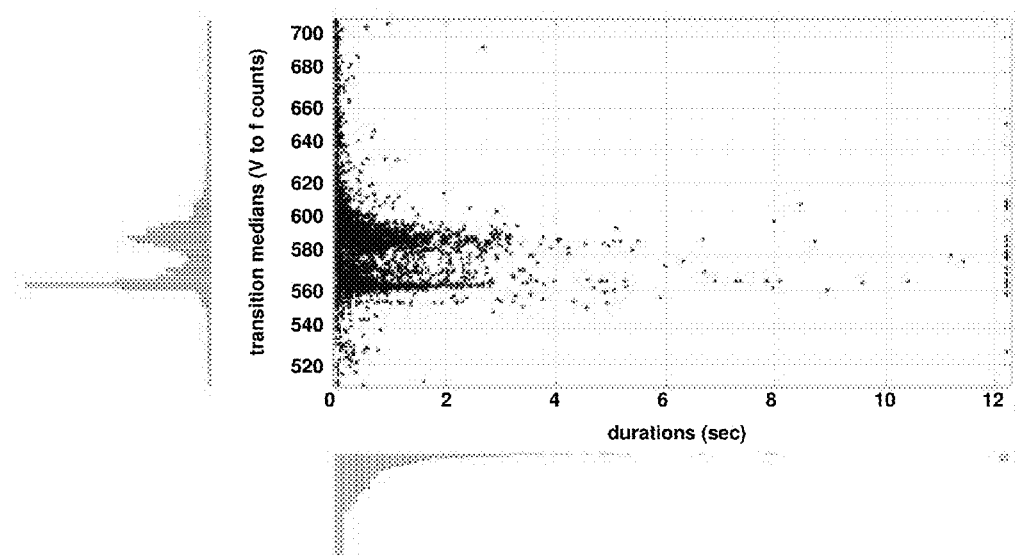
FIG. 14 illustrates the relationship between electric potential applied and dwelling time of speed bump-test DNA duplex in a nanopore.

Self-hybridized DNA-1 (2 µM), self-hybridized DNA-2 (2 µM), DNA-3 (2 µM), and streptavidin (1 µM) were incubated with multiple nanopores constructed as described supra for about 2 h at the working condition described supra in this example. An electric potential of about 128 mV was applied to the nanopore and electrical signals were collected and shown in FIG. 14. FIG. 14 showed that the 4-base duplex segments were able to stall DNA-1 and DNA-2 in the nanopore for a dwelling time of about 100 ms to 200 ms. These data showed that speed bumps as short as 4 bases worked to stall a ss test DNA long enough to obtain relevant sequence information.

Example 4

Stalling DNA by 6-Base Random Speed Bump Pool

This example illustrates a 6-base random speed bump pool successfully bound to, stalled in a nanopore detector and dissociated from a test DNA.

In this example, the ss test DNA was ss female genomic DNA. The random speed bump pool comprised hexamer DNA oligonucleotides having all combinations of the primary DNA nucleotides, which was purchased from Invitrogen.

The working condition was 20 mM HEPEs buffer and 1 M KCl at 0° C. The electric potential applied was about 128 mV.

The nanopores were created from 10 ng/mL alpha hemolysin deposited onto the surface of a bilayer at a final concentration of 0.2 ng/mL and with the application of electrical stimulus as described in US Application Publication No. 2011/0193570. The bilayers were created with the painting method from 10 mg/mL of DPhPC in Decane across the essentially planar AgCl electrode on a Teflon surface as described in US Application Publication No. 2011/0193570.

The ss test DNA (1 µM) was incubated with the 6-base random speed bump pool (100 µM) were incubated with multiple nanopores constructed as described supra for about 2 h at the working condition described supra in this example. An electric potential of about 128 mV was applied to the nanopore and electrical signals were collected. The signals showed that the 6-base random speed bump pool was able to bind to the ss test DNA, stall the ss test DNA in the nanopore long enough to obtain relevant sequence information, and dissociate from the ss test DNA as described herein.

What is claimed is:

1. A method for manipulating a nucleic acid molecule in a nanopore, the method comprising:
   (a) forming a first bulky structure on a first end of a nucleic acid molecule at a first temperature;
   (b) applying a first electrical potential to flow the nucleic acid molecule through a nanopore; and
   (c) forming a second bulky structure on a second end of the nucleic acid molecule at a second temperature.

2. The method of claim 1, wherein, said nucleic acid molecule is a single-stranded nucleic acid molecule, and wherein said method further comprises prior to (a):
   (a) providing a double-stranded nucleic acid molecule;
   (b) ligating a first pre-bulky structure to a first end of the double-stranded nucleic acid molecule; and
   (c) denaturing the double-stranded nucleic acid molecule of (f) to produce said single-stranded nucleic acid molecule.

3. The method of claim 2, wherein (e) further comprises ligating a second pre-bulky structure to a second end of the double-stranded nucleic acid molecule.

4. The method of claim 3, wherein the first pre-bulky structure and/or the second pre-bulky structure comprises a direction identifier.

5. The method of claim 3, wherein the second pre-bulky structure has a sequence of SEQ ID NO. 1.

6. The method of claim 1, further comprising, subsequent to (c), obtaining a first set of electrical signals while applying a second electrical potential to reverse the flow of the single-stranded nucleic acid molecule until the single-stranded nucleic acid molecule is stopped by the second bulky structure of step (c).

7. The method of claim 6, further comprising obtaining a second set of electrical signals while applying a third electrical potential to reverse the flow of the single-stranded nucleic acid molecule until the single-stranded nucleic acid molecule is stopped by the first bulky structure.

8. The method of claim 7, wherein said obtaining said first set of electrical signals and obtaining said second set of electrical signals are repeated.

9. The method of claim 8, wherein said obtaining said first set of electrical signals and obtaining said second set of electrical signals are repeated at least 10 times.

10. The method of claim 7, wherein the second and third electric potentials are the same.

11. The method of claim 7, wherein the second and third electric potentials are different.

12. The method of claim 7, wherein the second and/or third electric potentials are continuously changing.

13. The method of claim 6, wherein said first set of electrical signals are obtained at a third temperature.

14. The method of claim 13, wherein the first temperature is greater than the second temperature, and the second temperature is greater than the third temperature.

15. The method of claim 13, wherein the third temperature is from about −10 to 20° C.

16. The method of claim 1, wherein the first temperature is greater than the second temperature.

17. The method of claim 1, wherein said single-stranded nucleic acid molecule is contacted with one or more speed bumps.

18. The method of claim 17, wherein the one or more speed bumps comprise up to 12 nucleic acid bases.

19. The method of claim 17, wherein the one or more speed bumps comprise locked nucleotides, universal bases, dideoxy-nucleosides at the 3'end and/or the 5'end, morpholinos, glycol nucleotides, abasic nucleotides, methylated nucleobases, non-binding base mimics, or any combination thereof.

20. The method of claim 17, wherein an individual speed bump of the one or more speed bumps forms duplex sections with the single-stranded nucleic acid molecule, and the duplex sections have about the same melting temperatures.

21. The method of claim 17, wherein said one or more speed bumps are provided in a random speed bump pool.

22. The method of claim 21, wherein the random speed bump pool comprises speed bump trains formed by linking multiple speed bumps with non-binding linkers.

23. The method of claim 21, wherein said first bulky structure and/or said second bulky structure comprise non-binding structures that do not bind to the random speed bump pool.

24. The method of claim 23, wherein said non-binding structures are selected from the group consisting of isodG, isodC, abasic site and combinations thereof.

25. The method of claim 21, wherein said random speed bump pool comprises speed bumps having universal bases at a 3' end and/or a 5' end.

26. The method of claim 1, wherein the single-stranded nucleic acid molecule has a length from about 5 to 10,000 bases.

27. The method of claim 1, wherein the nanopore is an alpha hemolysin nanopore.

28. The method of claim 1, wherein said nanopore is in a membrane disposed adjacent or in proximity to an electrode.

29. A method for sequencing a nucleic acid molecule, comprising:
  (a) providing a chip comprising at least one nanopore in a lipid bilayer membrane that is disposed adjacent or in proximity to an electrode, wherein said electrode is adapted to detect said nucleic acid molecule or a portion thereof;
  (b) threading the nucleic acid molecule into the nanopore at a first temperature;
  (c) trapping the nucleic acid molecule in the nanopore at a second temperature; and
  (d) detecting one or more nucleic acid bases of the nucleic acid molecule while the nucleic acid molecule is trapped in the nanopore.

30. The method of claim 29, wherein the first temperature is greater than the second temperature.

31. The method of claim 29, wherein (d) is performed at a third temperature, and wherein the third temperature is lower than the first temperature and the second temperature.

32. The method of claim 29, wherein said detecting in (d) further comprises applying an electrical potential to reverse the flow of the nucleic acid molecule and obtaining a set of electrical signals.

33. The method of claim 32, wherein the nucleic acid molecule further comprises a bulky structure at an end of the nucleic acid molecule, and the flow of the nucleic acid molecule through said nanopore is stopped by the bulky structure.

34. The method of claim 33, further comprising applying another electrical potential to reverse the flow of the nucleic acid molecule and obtaining another set of electrical signals.

35. The method of claim 34, wherein the nucleic acid molecule further comprises another bulky structure at another end of the nucleic acid molecule, and the flow of the nucleic acid molecule through the nanopore is stopped by said another bulky structure.

36. The method of claim 29, wherein said nucleic acid molecule is trapped with the aid of a first bulky structure at a first portion of the nucleic acid molecule and a second bulky structure at a second portion of the nucleic acid molecule.

37. The method of claim 36, wherein trapping the nucleic acid molecule in (d) further comprises:
  i. forming said first bulky structure on said first portion of a nucleic acid molecule at the first temperature;
  ii. applying an electrical potential to thread the nucleic acid molecule into the nanopore; and
  iii. forming said second bulky structure on said second portion of the nucleic acid molecule at the second temperature.

38. The method of claim 37, wherein the first temperature is greater than the second temperature.

* * * * *

SEQUENCE LISTING

```
<160> NUMBER OF SEQ ID NOS: 6

<210> SEQ ID NO 1
<211> LENGTH: 24
<212> TYPE: DNA
<213> ORGANISM: Artificial Sequence
<220> FEATURE:
<223> OTHER INFORMATION: duplex hairpin structure

<400> SEQUENCE: 1 ccccccccc ttataccct ataa                                            24

<210> SEQ ID NO 2
<211> LENGTH: 34
<212> TYPE: DNA
<213> ORGANISM: Artificial Sequence
<220> FEATURE:
<223> OTHER INFORMATION: duplex hairpin structure

<400> SEQUENCE: 2
cgtctagcgt tgccgaaaac ggcaacgcta gacg                               34

<210> SEQ ID NO 3
<211> LENGTH: 35
<212> TYPE: DNA
<213> ORGANISM: Artificial Sequence
<220> FEATURE:
<223> OTHER INFORMATION: multi-hairpin structure

<400> SEQUENCE: 3
gaccctgccc ccagctttcc ccaaacgtca aaaaa                              35

<210> SEQ ID NO 4
<211> LENGTH: 14
<212> TYPE: DNA
<213> ORGANISM: Artificial Sequence
<220> FEATURE:
<223> OTHER INFORMATION: self-hybridizable structure

<400> SEQUENCE: 4 ccccccccc gcgc                                                      14

<210> SEQ ID NO 5
<211> LENGTH: 14
<212> TYPE: DNA
<213> ORGANISM: Artificial Sequence
```

-continued

```
<220> FEATURE:
<223> OTHER INFORMATION: self-hybridizable structure

<400> SEQUENCE: 5
tttttttttt gcgc                                                          14

<210> SEQ ID NO 6
<211> LENGTH: 40
<212> TYPE: DNA
<213> ORGANISM: Artificial Sequence
<220> FEATURE:
<223> OTHER INFORMATION: 3'-biotinylated structure

<400> SEQUENCE: 6
tttttttttt tttttttttt tttttttttt tttttttttt                              40
```